(12) United States Patent
Bobet et al.

(10) Patent No.: US 8,715,568 B2
(45) Date of Patent: May 6, 2014

(54) USE OF COMPOSITIONS CONTAINING SILICON FOR IMPROVING THE CORROSION RESISTANCE OF VESSELS

(75) Inventors: Josselin Bobet, Tavaux (FR); Christian Franck, Sterrebeek (BE)

(73) Assignee: Solvay SA, Brussels (BE)

( * ) Notice: Subject to any disclaimer, the term of this patent is extended or adjusted under 35 U.S.C. 154(b) by 702 days.

(21) Appl. No.: 12/681,083

(22) PCT Filed: Sep. 25, 2008

(86) PCT No.: PCT/EP2008/062845
§ 371 (c)(1),
(2), (4) Date: Mar. 31, 2010

(87) PCT Pub. No.: WO2009/043796
PCT Pub. Date: Apr. 9, 2009

(65) Prior Publication Data
US 2010/0212540 A1 Aug. 26, 2010

Related U.S. Application Data

(60) Provisional application No. 60/976,845, filed on Oct. 2, 2007.

(51) Int. Cl.
*C23F 11/00* (2006.01)
(52) U.S. Cl.
USPC .............................................. 422/7; 252/387
(58) Field of Classification Search
USPC ............................................ 252/387; 422/7
See application file for complete search history.

(56) References Cited

U.S. PATENT DOCUMENTS

| 280,893 | A | 7/1883 | Baujard |
| 865,727 | A | 9/1907 | Queneau |
| 2,060,715 | A | 11/1936 | Arvin |

(Continued)

FOREIGN PATENT DOCUMENTS

| BE | 422877 A | 8/1937 |
| CA | 2 375 245 | 12/2000 |

(Continued)

OTHER PUBLICATIONS

Herman A. Bruson, et al., "Thermal Decomposition of Glyceryl Carbonates," Journal of the American Chemical Society, vol. 74, Apr. 1952 pp. 2100-2101.

(Continued)

*Primary Examiner* — Monique Cole
(74) *Attorney, Agent, or Firm* — Oblon, Spivak, McClelland, Maier & Neustadt, L.L.P.

(57) ABSTRACT

Use of a composition comprising silicon, oxygen and at least one of calcium, potassium, or titanium, as a material for coating an equipment or as a constituent material of equipment, intended to be in contact with a mixture containing a chlorohydrin, hydrogen chloride and water. The use of the composition may provide a method for reducing corrosion of the equipment, for decreasing the frequency of replacement of the equipment and/or for lowering the risks linked to equipment breakage and leak. The equipment which is intended to be in contact with the mixture may be used in a process for manufacturing a chlorohydrin, in which a polyhydroxylated aliphatic hydrocarbon, an ester of a polyhydroxylated aliphatic hydrocarbon or a mixture of the two, is reacted with a chlorinating agent that contains hydrogen chloride.

10 Claims, 1 Drawing Sheet

(56) References Cited

U.S. PATENT DOCUMENTS

| | | |
|---|---|---|
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,463,850 A | 3/1949 | Brooks |
| 2,505,735 A | 4/1950 | Halbedel |
| 2,726,072 A | 12/1955 | Herman |
| 2,733,195 A | 1/1956 | Miller |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,879,180 A | 4/1975 | Hutgens et al. |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,104,434 A | 8/1978 | Johnson |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,294,776 A | 10/1981 | Hardy et al. |
| 4,309,394 A | 1/1982 | Hudson |
| 4,322,367 A | 3/1982 | Silvis |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,560,812 A | 12/1985 | Blytas |
| 4,595,469 A | 6/1986 | Foller |
| 4,599,178 A | 7/1986 | Blytas |
| 4,609,751 A | 9/1986 | Hajjar |
| 4,634,784 A | 1/1987 | Nagato et al. |
| 4,655,879 A | 4/1987 | Brockmann et al. |
| 4,877,497 A | 10/1989 | Watanabe et al. |
| 4,898,644 A | 2/1990 | Van Horn |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer et al. |
| 5,567,359 A | 10/1996 | Cassidy et al. |
| 5,578,740 A | 11/1996 | Au et al. |
| 5,679,839 A | 10/1997 | Armand et al. |
| 5,710,350 A | 1/1998 | Jeromin et al. |
| 5,731,476 A | 3/1998 | Shawl et al. |
| 5,744,655 A | 4/1998 | Thomas et al. |
| 5,766,270 A | 6/1998 | Neuman et al. |
| 5,779,915 A | 7/1998 | Becker et al. |
| 5,908,946 A | 6/1999 | Stern et al. |
| 5,955,043 A | 9/1999 | Neuman et al. |
| 5,993,974 A | 11/1999 | Fukushima et al. |
| 6,001,494 A * | 12/1999 | Kuchinski et al. ............ 428/653 |
| 6,024,839 A | 2/2000 | Schufeldt |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,428,759 B1 | 8/2002 | Smith et al. |
| 6,521,794 B2 | 2/2003 | Hirota |
| 6,589,497 B2 | 7/2003 | Smith |
| 6,719,957 B2 | 4/2004 | Brady, Jr. et al. |
| 6,740,633 B2 | 5/2004 | Norenberg et al. |
| 6,806,396 B2 | 10/2004 | Gelblum et al. |
| 6,831,201 B2 | 12/2004 | Katsuura et al. |
| 7,126,032 B1 | 10/2006 | Aiken |
| 7,128,890 B2 | 10/2006 | Ollivier |
| 7,453,008 B2 | 11/2008 | Ko et al. |
| 7,584,629 B2 | 9/2009 | Sohn et al. |
| 7,619,056 B2 | 11/2009 | East et al. |
| 8,106,246 B2 | 1/2012 | Krafft et al. |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0170122 A1 | 7/2007 | Tabata et al. |
| 2007/0251831 A1 | 11/2007 | Kaczur et al. |
| 2007/0293707 A1 | 12/2007 | Wolfert et al. |
| 2008/0021209 A1 | 1/2008 | East et al. |
| 2008/0053836 A1 | 3/2008 | Bulan et al. |
| 2008/0146753 A1 | 6/2008 | Woike et al. |
| 2008/0214848 A1 | 9/2008 | Krafft et al. |
| 2009/0022653 A1 | 1/2009 | Strebelle et al. |
| 2009/0173636 A1 | 7/2009 | Ooms et al. |
| 2009/0198041 A1 | 8/2009 | Krafft et al. |
| 2010/0029959 A1 | 2/2010 | Fan et al. |
| 2010/0305271 A1 | 12/2010 | Mentink et al. |
| 2010/0311874 A1 | 12/2010 | Mentink et al. |
| 2010/0311905 A1 | 12/2010 | Mentink et al. |
| 2011/0086949 A1 | 4/2011 | Mentink et al. |
| 2011/0118390 A1 | 5/2011 | Feron et al. |
| 2011/0195148 A1 | 8/2011 | Mentink et al. |
| 2012/0010420 A1 | 1/2012 | Gilbeau et al. |
| 2012/0199493 A1 | 8/2012 | Krafft et al. |
| 2012/0199786 A1 | 8/2012 | Gilbeau |

FOREIGN PATENT DOCUMENTS

| | | |
|---|---|---|
| CN | 1135533 | 11/1996 |
| CN | 1296003 A | 5/2001 |
| CN | 101041421 | 9/2007 |

(56) References Cited

FOREIGN PATENT DOCUMENTS

| | | |
|---|---:|---:|
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 955 233 | 1/1957 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 43 02 306 | 8/1994 |
| DE | 4335311 A1 | 4/1995 |
| DE | 10203914 C1 | 10/2003 |
| DE | 10254709 A1 | 6/2004 |
| EP | 0 296 341 | 12/1988 |
| EP | 0 317 184 | 5/1989 |
| EP | 0 317 185 | 5/1989 |
| EP | 0347618 A2 | 12/1989 |
| EP | 0358255 A1 | 3/1990 |
| EP | 0421379 A1 | 4/1991 |
| EP | 0 452 265 | 10/1991 |
| EP | 0518765 A1 | 12/1992 |
| EP | 0522382 A1 | 1/1993 |
| EP | 0535949 B1 | 4/1993 |
| EP | 0561441 A1 | 9/1993 |
| EP | 0563720 A1 | 10/1993 |
| EP | 0568389 A1 | 11/1993 |
| EP | 0582201 A2 | 2/1994 |
| EP | 0 618 170 | 10/1994 |
| EP | 0 916 624 | 5/1999 |
| EP | 0919551 A1 | 6/1999 |
| EP | 0 774 450 | 2/2000 |
| EP | 0 979 671 | 2/2000 |
| EP | 1059278 A2 | 12/2000 |
| EP | 1106237 A1 | 6/2001 |
| EP | 1153887 A2 | 11/2001 |
| EP | 1163946 A1 | 12/2001 |
| EP | 1231189 A1 | 8/2002 |
| EP | 1298154 A1 | 4/2003 |
| EP | 1411027 A1 | 4/2004 |
| EP | 1752435 A1 | 2/2007 |
| EP | 1752436 A1 | 2/2007 |
| EP | 1760060 A1 | 3/2007 |
| EP | 1762556 A1 | 3/2007 |
| EP | 1770081 A1 | 4/2007 |
| EP | 1772446 A1 | 4/2007 |
| EP | 1775278 A1 | 4/2007 |
| EP | 2085364 | 8/2009 |
| FR | 1 056 360 | 2/1954 |
| FR | 1 306 231 | 10/1961 |
| FR | 1 417 388 | 10/1964 |
| FR | 1476073 A | 4/1967 |
| FR | 1 577 792 | 8/1968 |
| FR | 2151107 | 4/1973 |
| FR | 2180138 | 5/1973 |
| FR | 2 217 372 | 2/1974 |
| FR | 2565229 A1 | 12/1985 |
| FR | 2752242 A1 | 2/1998 |
| FR | 2862644 A1 | 5/2005 |
| FR | 2868419 A1 | 10/2005 |
| FR | 2869612 A1 | 11/2005 |
| FR | 2869613 A1 | 11/2005 |
| FR | 2872504 A1 | 1/2006 |
| FR | 2881732 A1 | 8/2006 |
| FR | 2885903 A1 | 11/2006 |
| FR | 2 912 743 | 8/2008 |
| FR | 2913683 | 9/2008 |
| FR | 2913683 A1 | 9/2008 |
| FR | 2 917 411 | 12/2008 |
| FR | 2918058 A1 | 1/2009 |
| FR | 2925045 A1 | 6/2009 |
| FR | 2 927 083 | 8/2009 |
| FR | 2929611 A1 | 10/2009 |
| FR | 2935699 A1 | 3/2010 |
| FR | 2935968 A1 | 3/2010 |
| GB | 14767 A | 0/1914 |
| GB | 406345 | 8/1932 |
| GB | 404938 A | 1/1934 |
| GB | 467481 A | 6/1937 |
| GB | 541357 A | 11/1941 |
| GB | 724222 | 6/1952 |
| GB | 679536 A | 9/1952 |
| GB | 702143 A | 1/1954 |
| GB | 758665 | 10/1954 |
| GB | 736641 A | 9/1955 |
| GB | 799567 A | 8/1958 |
| GB | 984446 A | 2/1965 |
| GB | 984633 A | 3/1965 |
| GB | 1046521 A | 10/1966 |
| GB | 1083594 A | 9/1967 |
| GB | 1286893 A | 8/1972 |
| GB | 1387668 A | 3/1975 |
| GB | 1 493 538 | 4/1975 |
| GB | 1414976 A | 11/1975 |
| GB | 2173496 A | 10/1986 |
| GB | 2336584 A | 10/1999 |
| HU | 2002-003023 | 3/2004 |
| JP | 3927230 B2 | 11/1939 |
| JP | 50-062909 | 5/1975 |
| JP | 51021635 B | 7/1976 |
| JP | 55041858 A | 3/1980 |
| JP | 5629572 | 3/1981 |
| JP | 5699432 | 8/1981 |
| JP | 56-155009 | 12/1981 |
| JP | 60-258171 | 12/1985 |
| JP | 61-044833 | 3/1986 |
| JP | 61 112066 A | 5/1986 |
| JP | 61-140532 | 6/1986 |
| JP | 61236749 A | 10/1986 |
| JP | 61-120688 | 6/1987 |
| JP | 62242638 A | 10/1987 |
| JP | 62-278290 | 12/1987 |
| JP | 63195288 A | 8/1988 |
| JP | 2-137704 | 5/1990 |
| JP | 03014527 A | 1/1991 |
| JP | 3223267 A | 10/1991 |
| JP | 03223267 A | 10/1991 |
| JP | 04089440 A | 3/1992 |
| JP | 04-217637 | 8/1992 |
| JP | 06-009589 | 1/1994 |
| JP | 625196 B2 | 4/1994 |
| JP | 06184024 A | 7/1994 |
| JP | 6321852 A | 11/1994 |
| JP | 08-003087 | 1/1996 |
| JP | 859593 | 3/1996 |
| JP | 09-2999953 | 11/1997 |
| JP | 10139700 A | 5/1998 |
| JP | 10218810 A | 8/1998 |
| JP | 1998218810 A | 8/1998 |
| JP | 20000344692 A | 12/2000 |
| JP | 2001-037469 | 2/2001 |
| JP | 2001-213827 A | 8/2001 |
| JP | 2001-261308 | 9/2001 |
| JP | 2001-1261581 A | 9/2001 |
| JP | 2001-276572 | 10/2001 |
| JP | 2002-02033 A2 | 1/2002 |
| JP | 20020038195 A | 2/2002 |
| JP | 2002-256494 | 9/2002 |
| JP | 20020265986 A | 9/2002 |
| JP | 2002-363153 A | 12/2002 |
| JP | 2003-502154 | 1/2003 |
| JP | 2003-89680 A | 3/2003 |
| JP | 2003081891 A | 3/2003 |
| JP | 2003-183191 | 7/2003 |
| JP | 2003-206473 | 7/2003 |
| JP | 2004-130263 | 4/2004 |
| JP | 2004-518102 | 6/2004 |
| JP | 2004-216246 | 8/2004 |

(56) References Cited

FOREIGN PATENT DOCUMENTS

| | | |
|---|---|---|
| JP | 2005007841 A2 | 1/2005 |
| JP | 2005097177 A2 | 4/2005 |
| JP | 2005-513064 | 5/2005 |
| JP | 2005-154292 | 6/2005 |
| JP | 2006-052434 | 2/2006 |
| JP | 2007-008898 | 1/2007 |
| JP | 2007-185578 | 7/2007 |
| JP | 2009-263338 | 11/2009 |
| KR | 900006513 | 11/1987 |
| KR | 1019920003099 B1 | 4/1992 |
| KR | 10-514819 B1 | 9/2005 |
| PL | 136598 | 3/1986 |
| PL | 162910 | 1/1994 |
| SU | 123153 | 1/1959 |
| SU | 1125226 | 11/1984 |
| SU | 1159716 | 6/1985 |
| SU | 1685969 | 10/1991 |
| WO | WO 95/14635 | 6/1995 |
| WO | WO 95/14639 | 6/1995 |
| WO | WO 96/15980 | 5/1996 |
| WO | WO 97/48667 | 12/1997 |
| WO | WO 96/07617 | 3/1998 |
| WO | WO 98/37024 | 8/1998 |
| WO | WO 99/14208 | 3/1999 |
| WO | WO 9932397 A1 | 7/1999 |
| WO | WO 0024674 A1 | 5/2000 |
| WO | WO 01/43762 | 6/2001 |
| WO | WO 0141919 A1 | 6/2001 |
| WO | WO 0186220 A2 | 11/2001 |
| WO | WO 02/26672 A2 | 4/2002 |
| WO | WO 02/059536 | 8/2002 |
| WO | WO 03/064357 | 8/2003 |
| WO | WO 2004/056758 | 7/2004 |
| WO | WO 2005021476 A1 | 3/2005 |
| WO | WO 2005054167 A1 | 6/2005 |
| WO | WO 2005/075189 | 8/2005 |
| WO | WO 2005/097722 | 10/2005 |
| WO | WO 2005/115954 | 12/2005 |
| WO | WO 2005/116004 | 12/2005 |
| WO | WO 2006020234 A1 | 2/2006 |
| WO | WO 2006/100311 A2 | 9/2006 |
| WO | WO 2006/100312 A2 | 9/2006 |
| WO | WO 2006/100313 A2 | 9/2006 |
| WO | WO 2006/100314 A1 | 9/2006 |
| WO | WO 2006/100315 A2 | 9/2006 |
| WO | WO 2006/100316 A1 | 9/2006 |
| WO | WO 2006/100317 A1 | 9/2006 |
| WO | WO 2006/100318 A2 | 9/2006 |
| WO | WO 2006/100319 A1 | 9/2006 |
| WO | WO 2006/100320 A2 | 9/2006 |
| WO | WO 2006/106153 A2 | 10/2006 |
| WO | WO 2006/106154 A1 | 10/2006 |
| WO | WO 2006/106155 A2 | 10/2006 |
| WO | WO 2007/054505 A2 | 5/2007 |
| WO | WO2007/144335 | 12/2007 |
| WO | WO 2008/101866 | 8/2008 |
| WO | WO2008/107468 | 9/2008 |
| WO | WO 2008/110588 | 9/2008 |
| WO | WO2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO2009/000773 | 12/2008 |
| WO | WO 2009/016149 A2 | 2/2009 |
| WO | WO 2009026212 A1 | 2/2009 |
| WO | WO2009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO 2009/095617 | 8/2009 |
| WO | WO 2009/095618 | 8/2009 |
| WO | WO 2009/095622 | 8/2009 |
| WO | WO2009/121853 A1 | 10/2009 |
| WO | WO 2009/121853 | 10/2009 |
| WO | WO 2009/150385 | 12/2009 |
| WO | WO 2010/010282 | 1/2010 |
| WO | WO 2010/029039 | 3/2010 |
| WO | WO 2010/029039 A1 | 3/2010 |
| WO | WO 2010/029153 | 3/2010 |
| WO | WO 2010/029153 A1 | 3/2010 |
| WO | WO 2010/043813 | 4/2010 |
| WO | WO 2010/066660 | 6/2010 |
| WO | WO 2010/136725 | 12/2010 |
| WO | WO 2011/054769 | 5/2011 |
| WO | WO 2011/054770 | 5/2011 |
| WO | WO 2012/016872 | 2/2012 |
| WO | WO 2012/025468 | 3/2012 |
| WO | WO 2012/041816 | 4/2012 |
| WO | WO 2012/056005 | 5/2012 |

OTHER PUBLICATIONS

Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1988, pp. 354-360.
Application No. FR 06.05325 filed Jun. 14, 2006 by Solvay S.A.-priority document to EP2007/55742 published as WO 2007/144335 17 pgs.
Application No. FR 07.53863 filed Mar. 15, 2007 by Solvay S.A. and published as FR2913683, 19 pgs (attached herein)-priority document to EP2007/55742 published as WO2007/144335 29 pgs.
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.
Rudnenko, EV, et al., 1988, Lakokrasochnye Materially i 1kh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.

(56) References Cited

OTHER PUBLICATIONS

Jeffrey Lutje Spelberg, et al, A Tandem Enzyme Reaction to Produce Optically Active Halohydrins, Epoxides and Diols, Tetrahedron: Asymmetry, Elsevier Science Publishers, vol. 10, No. 15, 1999, pp. 2863-2870.
Oleoline.com. Glycerine Market report, Sep. 10, 2003, No. 62, 31 pgs.
Notification Under Act. No. 100/2001, Coll. As Amended by Act No. 93/2004, Coll. to the extent of Annex No. 4 (SPOLEK) Nov. 30, 2004, 80 pgs.
Documentation Under Act. No. 100/2001 Coll. As Amended by Act. No. 93/2004 Coll in the scope of appendix No. 4 (SPOLEK) Jan. 11, 2005, 86 pgs.
K. Weissermel & H.J. Arpe, Industrial Organic Chemistry, Third, Completely Revised Edition, VCH, 1997, pp. 149 & 275.
Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.
The Merck Index, Eleventh Edition, 1989, pp. 759-760.
Ullmann's Encyclopedia of Industrial Chemistry, Fifth completely Revised Edition, vol. A1, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.
K. Weissermel & H.J. Arpe, Industrial Organic Chemistry, Third, Completely Revised Edition, VCH 1997, pp. 149-163.
K. Weissermel & H.J. Arpe, in Industrial Organic Chemistry, Third, Completely Revised Edition, VCH 1997, pp. 275-276.
Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and similar passages but retrieved from the English Fifth Edition of the Book, 1987).
Perry's Chemical Engineers' Handbook, Sixth Edition, Robert H. Perry, Don Green, 1984, Section 21-64 to 21-68.
Iwanami et al, Dictionary of Physics and Chemistry, Third Edition, Ryo Midorikawa /Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll., as amended by later regulations of the project/intent combined project for the manufacture of epichlorohydrin (SPOLEK) Apr. 2005.
Kirk Othmer Encyclopedia of Chemical Technology, Third Edition, vol. 12, 1980, pp. 1002-1005.
Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.
Product Brochure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Catalogue of Nittetu Chemical Engineering Ltd. (Published in Mar. 1994).
12093 Chemicals, The Chemical Daily Co., Ltd. (Published on Jan. 22, 1993) with attached English translation of relevant excerpts, 24 pgs.
Chemicals Guide, Chemical Daily Co., Ltd. (Published on Jun. 15, 1990) with attached English translation of relevant excerpts.
Ma Zengxin et al, "recovery of Polyglycerol from residues of Synthetic Glycerol" Riyong Huaxue Gongye, 1997, 4, 21023 (English Abstract only).
Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.
Production and Prospect of the World Natural Glycerol by Zhu Shiyong, Cereals and Oils, vol. 1, 1997, pp. 33-38 (No English Translation).
Vinnolit; Vinnolit receives EU grant for water recycling project; Press Release, 2008: http://www.vinnolit.de/vinnolit.nsf/id/EN_Vinnolit_receives_EU_grant_for_water_recycling_project_.
N.W. Ziels, Journal of American Oil Chemists' Society, Nov. 1956, vol. 33, pp. 556-565.
Perry's Chemical Engineers Handbook, Sixth Edition, McGraw Hill Inc., (1984) Section 18.
vol. B3: Unit Operations II of Ullmann's Encyclopedia of Industrial Chemistry, Fifth Completely Revised Edition, Published by VCH, 1988.
W. Giger et al., "14C/12C-Ratios in Organic Matter and Hydrocarbons Extracted from Dated Lake Sediments," Nuclear Instruments and Methods in Physics Research B5 (1984), 394-397, XP-002631954.
Jurgen O. Metzger, "Fats and Oils as Renewable Feedstock for Chemistry," Eur. J. Lipid Sci. Technol. (2009), 111, 865-876. XP-002631953.
Bruce M. Bell, "Glycerin as a Renewable Feedstock for Epichlorohydrin Production. The GTE Process," Clean-Soil, Air, and Water, vol. 36, No. 8, (2008) pp. 657-661, XP-002631952.
J.B. Conant, et al, "Glycerol a,y-dichlorohydrin", Organic Syntheses Coll., 1941, vol. 1, p. 292-294 (5 pp.).
Gilman H., Organic Synthesis, Section 1, pp. 234-235 (no date)—attached English translation only.
Industrial Chemical Encyclopedia 5, p. 457 (no date)—attached English translation only.
"Epoxy resins", p. 36-46, by Shangai Resin Plant, Shangai People's Press, 1971—attached English translation only.
Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.
"Rainwater Harvesting and Utilization" (United Nations Environment Program) Mar. 2002; XP003003726; Internet Citation extracted online on Jan. 1, 2006: URL:http://www.unep.or.jp/letc/Publication—4 pp.
Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.
Myszkowski, J. et al. "Removal of organic compounds from gaseous hydrogen chloride by an absorption method" Chemia Stosowana (1986) vol. 30(4) p. 545-551; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.
Laine, D.F. et al. "The destruction of organic pollutants under mild reaction conditions; a review" Michochemical Journal, vol. 85, No. 2, 2007 pp. 183-193; available online Aug. 17, 2006; 12 pp.
[Unknown Author], Kirk Othmer Encyclopedia of Chemical Technology—vol. 2, p. 156, John Wiley and Sons, 1992.
RD 436093, Aug. 10, 2000, Akzo Nobel.
Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).
Encyclopedia of Experimental Chemistry I, Basic Operation I, edited by The Chemical Society of Japan, Maruzen Co., Ltd., Nov. 5, 1990, 4th Edition, pp. 161 to 165 and 184 to 191 (no English translation available.
Encyclopedia of Chemistry 3, edited by Editorial Committee of Encyclopedia of Chemistry, Kyoritsu Shuppan Co., Ltd., Sep. 30, 1960, 1st Edition, 1st printing, pp. 312 and 313 (no English translation available).
Clarke et al., Org Synth., col. vol. 1, p. 233-234, 1964.

(56) References Cited

OTHER PUBLICATIONS

Braun, Org. Synth., col., vol. 2, p. 256-259, 1957.
Kirk Othmer Encyclopedia of Chemical Technology, 3rd Edition, vol. 9, pp. 267-289, 1980.
[Unknown Author]—New Experimental Chemical Course 1, Basic Operation I, Section 4, Separation and Purification, pp. 251-252 (issued on Sep. 20, 1975) with English translation from Shiga International Patent Office, 3 pgs.
March, Jerry—"Reactions, Mechanisms & Structure", Advanced Organic Chemistry, $4^{th}$ Ed., 1992, pp. 889, 908 and 937; 5 pgs.
[Unknown Author]—Bulletin de la Société Chimique de Paris— "Analyse des Travaux de Chimie Pure et Appliquée", G. Masson, Editor, Paris, Jul. 4, 1873, Novelle Série, Tome XIX, pp. 97-99; 4 pgs; comments regarding Friedel & Silva's work on middle of p. 98.
Neuberg, Irene Stephanie—"A New Way of Preparing Glyceraldehyde from Glycerol", Kaiser Wilhelm Institute in Berlin for Biochemi-Dahlem, 1930; 3 pgs; Includes abstract in English.
Krausz, Francois—'Recherches sur les Aldehydes Substitues en α en β. α and β Substituted Aldehydes', University Strasbourg, France ; Ann Chim 12, Nov.-Dec. 1949, 4, pp. 811-831, 23 pgs ; Includes abstract in English.
[Unknown Author]—"Glycerine—An Overview"—by the Soap and Detergent Association, Glycerine and Oleochemical Division, 1990; 27 pgs.
[Unknown Author]—"Commercial Synthesis of Glycerol Begins a New Shell Chemical Corp Plant—a staff Report"; Chemical & Engineering News, 1948, vol. 26, No. 38, pp. 2770-2771; 2 pgs.
Fairbourne, Arthur, et al—"The Partial Esterification of Polyhydric Alcohols . Part XII . The Funstion of Ethylene-oxide Rings", J. Chem. Soc. 1932, republished 1965, pp. 1965-1972; 8 pgs.
Clarke, H.T., et al—"Epichlorohydrin", Organic Syntheses, col. vol. 1, pp. 233 (1941) ; vol. 3, p. 47 (1923); 2 pgs.
Braun, Geza—"Epichlorohydrin and Epibromohydrin", Organic Syntheses, col. vol. 2, p. 256 (1943) ; vol. 16, p. 30 (1936); 2 pgs.
Conant, J.B., et al—"Glycerol a,y-Dichlorohydrin", Organic Syntheses, col. vol. 1, p. 292 (1941); vol. 2, p. 29 (1922); 3 pgs.
Chavanne, G.—"Memoires Presentes a La Societe Chimique", English translation—"Reports Submitted to Chemical Firm", Bull. Soc. Chim. Fr. 1943, 1, EP 06 121 086; 16 pgs.
Schroder, Angela, et al—"Glycerol as a by-product of biodiesel production in Diets for ruminants", 1999, The Regional Institute, Institute of Animal Nutrition, Physiology and Metabolism, University of Kiel, Germany, 6 pgs.
[Unknown Author]—"Chemical Properties and Derivatives of Glycerol ", 1965, Glycerine Producer's Association, $1^{st}$ Edition, 23 pgs.
Busby, G.W., et al—"The Purification of Glycerin by Ion-Exchange", The Journal of the American Oil Chemists' Society, 1952, 3 pgs.
Lamborn, Leebert Lloyd—"Modern Soaps, Candles and Glycerin", $3^{rd}$ Edition, 1918, D. Van Nostrand Company, London, 12 pgs.
Knothe, Gerhard—"Historical perspectives on vegetable oil-based diesel fuels", Industrial Oils, 2001, vol. 12, pp. 1103-1107; 5 pgs.
Schuchardt, Ulf, et al—"Transesterification of Vegetable Oils: a Review", 1998, Braz. Chem Soc., vol. 9, No. 1, pp. 199-210; 12 pgs.
Claude, Sylvain—"Research of new outlets of glycerol-recent developments in France"—1999, Fett/Lipid, No. 3, Wiley-VCH Verlag GmbH, Weinheim, pp. 101-104; 4 pgs.
Prakash, Chandra B.—"A Critical Review of Biodiesel as a Transportation Fuel in Canada", 1998, GCSI—Global Change Strategies International Inc.; 119 pgs.
Fukuda, Hideki, et al—"Review—Biodiesel Fuel Production by Transesterification of Oils", 2001, Journal of Bioscience and Bioengineering; vol. 92, No. 5, pp. 405-416; 12 pgs.
Yong, K.C., et al—"Refining of Crude Glycerine Recovered From Glycerol Residue by Simple Vacuum Distillation", Dec. 2001, Journal of Oil Palm Research, vol. 13, No. 2, pp. 39-44, 6 pgs.
Horsley, Lee H.—"Azeotropic Data-III", The Dow Chemical Co., Midland, MI, American Chemical Society 1973; pp. 1-4; 4 pgs.
Suzawa, Yoshikazu, et al—"Incineration System for Waste Liquid Containing Chlorinated Organic Compounds", Chemical Apparatuses, 1981, vol. 23, No. 11; 34 pgs; Translation in English provided.
D'Alonzo, R.P., et al—"Glyceride Composition of Processed Fats and Oils As Determined by Glass Capillary Gas Chromatography", Journal of American Oil Chemists' Society, 1982, vol. 59, No. 7, pp. 292-295; 4 pgs.
Chemical Engineering Handbook, $6^{th}$ Revised Edition, 2001, pp. 1-36; 56 pgs; Translation in English provided.
"Electrolytic cell test for electrolysis of epoxy sewage salt to prepare chlor-alkali", Process Equipment Department of Research Institute of Chloro-Alkali, Shengyang Chemical Plant, Liaoning Chemical Industry, Issue n° 2, pp. 32-37, published Dec. 31, 1981; 17 pgs; Translation in English provided.
Chengxin, Ren, et al—"Analysis on the Composition of the Byproduct During the Manufacturing Process of S-Epichlorohydrin by GC-MS", Chemical Analysis and Meterage, 2003, vol. 12, Issue No. 3, pp. 25-26; 6 pgs; Translation in English provided.
Encyclopedia of Chemical Technology, vol. 5, Nov. 1993; 6 pgs; Translation in English provided.
"Manufacture and use of epoxy resin", edited by Shanghai Resin Factory, published by China Petrochemical Press, First Edition, Oct. 1974; 16 pgs; Translation in English provided.
Gilman, Henry, et al—"Organic synthesis", Part 1, published by Scientific Publishing, 1957 (with abstract); 4 pgs.
Handbook of Chemical Products, Heavy Organic Chemicals, Second edition, published by Chemical Industry Press, Jan. 1995; 13 pgs; Translation in English provided.
Kiseleva, R. A., et al—"Study of the Interaction of Dibasic Acids with Glycerol", J. App. Chem. USSR, 1971, vol. 44, pp. 2086-2090; 5 pgs.
Handbook of Corrosion Data and Material Selection, published by Chemical Industry Press, edited by Jingyi Zuo, Yu Zuo; First edition, Oct. 1995, 5 pgs; Translation in English provided.
Handbook of Azeotropic Mixture, edited by Information Department of Comprehensive Scientific Technology Research Institution of Fushun City, 1993; 8 pgs; Translation in English provided.
"Industry Chemical Reaction and Application", published by Chinese Scientific Technology University Press, 1999; 4 pgs; Translation in English provided.
"Epoxy resin", published by Shanghai People's Publishing House, 1971; Translation in English provided; 21 pgs.
Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the American Chemical Society, 1956, vol. 78, pp. 4921-4925; 5 pgs.
Encyclopedia for Chinese Adult Education, 1994, p. 623; 10 pgs; Translation in English provided.
Perry's Chemical Engineers Handbook, Sixth Edition, Mc Graw Hill Inc., 1984, Section 14 (pp. 14-1-14-40).
Perry's Chemical Engineers Handbook, Sixth Edition, Mc Graw Hill Inc., 1984, Section 22-32 to 22-37.
U.S. Appl. No. 13/818,753, filed Feb. 25, 2013, Gilbeau, et al.
Kaszonyi A. et al., "Bioglycerol a new platform chemical", in 44th International Petroleum Conference, 2009, 8 p.. Bratislava, Slovak Republic.
Williamson R. et al., "DE-FC36-03GO1300 Final Report: Continuous Isosorbide Production from Sorbitol using Solid Acid Catalysis", 2006, 9 p., DOE Award for Iowa Corn Promotion Board.
Malhotra S. V. et al., "Applications of Corn-Based Chemistry", in The Bridge Publication of the National Academy of Engineering, 2007, V 34, No. 4, 8 p.
Jaffe M. et al., "Corn (Sugars) Based Chemistries for the Polymer Industry", in ANTEC 2009, 67th Annual Technical Conf., Proceed., Society of Plastic Engineers, Jun. 22-24, Mc Cormick, Place West Chigaco, Illinois.
Anon., "Iowa Corn Promotion Board, NJIT to License Breakthrough, Safe Bio-Plastic Alternative", New Jersey Science & Technology University press release, Aug. 6, 2008.
Anon., "NJIT Patent May Be Able to Replace BPA; Make Consumer Products Safer", New Jersey Science & Technology University press release, Feb. 4, 2010.

(56) References Cited

OTHER PUBLICATIONS

Fenouillot F. et al, "Polymers from renewable 1,4:3,6-dianhydrohexitols (isosorbide isomannide and isoidide): a Review", in Progress in Polymer Science, 2010, V 35, N 5, p. 578-622.
U.S. Appl. No. 13/832,363, filed Mar. 15, 2013, Krafft, et al.
U.S. Appl. No. 13/876,003, filed Mar. 26, 2013, Gilbeau, et al.
U.S. Appl. No. 13/878,429, filed Apr. 9, 2013, Balthasart, et al.
Trent et al., "Reactive Stripping in a Rotating Packed Bed for the Production of Hypochlorous Acid", *BHR Group*, Conference Series Publication (1999), 38 (Process Intensification for the Chemical Industry), 217-231.
M. Vajda et al., Membrane-Based Extraction Joined With Membrane-Based Stripping in a Circulating Arrangement II. Extraction of Organic Acids, *Chemical Papers*, (2003), 57(1), 3-10.
U.S. Appl. No. 13/623,979, filed Sep. 21, 2012, Gilbeau.
U.S. Appl. No. 13/755,236, filed Jan. 31, 2013, Krafft, et al.
U.S. Appl. No. 13/709,218, filed Dec. 10, 2012, Boulos, et al.
U.S. Appl. No. 13/813,348, filed Jan. 30, 2013, Gilbeau, et a.
Wu, Guoying, et al., "Preparation of Biodiesel and Glycerol by Methyl Esterification of Cottonseed Oil," China Oil and Fat, (2003), vol. 28, Iss. 4, 70-73, pp. 1-9.
Zhu Shiyong, "Production and Prospects of the World's Natural Glycerin," Cereals and Oils, (1997), Issue 01, 33-38, pp. 1-15.
Arthur J. Hill et al, "A Synthesis of Beta-Chloro-Ally Chloride," Journal American Chemical Society, 1922, 44(11), 2582-2595.
Physical and Chemical Dictionary (5th Edition), Feb. 20, 1998 (with attached English translation of cited excerpt).
Encyclopaedia Chimica, No. 8, $1^{st}$ Edition, Feb. 28, 1962 1-1, (with attached English translation of cited excerpt).
Encyclopaedia Chimica, No. 2, $1^{st}$ Edition, Jun. 30, 1960, 1-2, (with attached English translation of cited excerpt).
Klaus Gottlieb, et al., "Glycerine—a Sustainable Raw Material," Chem. Ing. Tech. 66 (1994) Nr.1, S, 64-66 (with attached English translation).
Wissenschaft & Technik, Mar. 1995, pp. 139-142 (no translation).
Milchert et al., "Dehydrochlorination of Glycerol Dichlorohydrin to Epichlorohydrin," *Chem. Papers*, 49 (3) 133-136 (1995).
M. Demarquay, "De La Glycerine," Librairie de la Faculte de Medecine, Paris 1863 (no translation).
Perry's Chemical Engineers Handbook, $7^{th}$ Edition, Section 28, pp. 28-1 to 28-64 (1997).
Perry's Chemical Engineers Handbook, 6th Edition, Section 23, pp. 23-16, 23-17, 23-26 and 23-38 (1984).
Dupont Teflon PTFE, Fluoropolymer Resin, Properties Handbook, (published Jul. 1996).
Chemical Process and Design Handbook, James Speight, 2002, McGraw-Hill, pp. 1,21-1,23.
Ullmanns Encyklopädie der Technischen Chemie, Band 12, pp. 367-375, Verlag Chemie GmbH, Weinheim/Bergstr, 1976, (A3) (no English translation).
Keith Schroeder, "Glycerine", bailey's Industrial Oil and Fats Products, 6th ed, 2005, pp. 191-222.
Apparate Technik—Bau—Anwendung, 2, Ausgabe, Vulkan Verlag Essen 1997, Thier (no English translation).
Auswahlkritieren fur Aiskleidungen mit Flurkunstoffen, Chemie Technik 1991, 4, S 31-29, Werthmüller (no English translation).
Summary of the difference between the following documents: Citation 3: Japanese Examined Patent Application, Second Publication No. S50-8454 Citation 3': United Kingdom Patent No. 1 286 893 (Corresponding English language application of Citation 3).
Ullmann's Encyclopedia Industrial Chemistry, $5^{th}$ Ed. vol. A6 (1988) pp. 401-477.
Polymer Science Dictionary, M.S.M., Elsevier Applied Chemistry, London & New York, 1989 p. 86.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz. Wasser, Abwasser 200 (Wissenschaftlich-technische Mitteilungen des Instituts Zur Foerderung der Wasserguerte- und Wasser-rnengenwirtschaft e; V; -2005 p. 81/-8/5., vol. 5.
Klaus Weissermel, et al., "Industrial Organic Chemistry," ($3^{rd}$ Completely Revised Edition); VCH 1997. p. 93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997. p. 347-355.
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).
M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.

\* cited by examiner

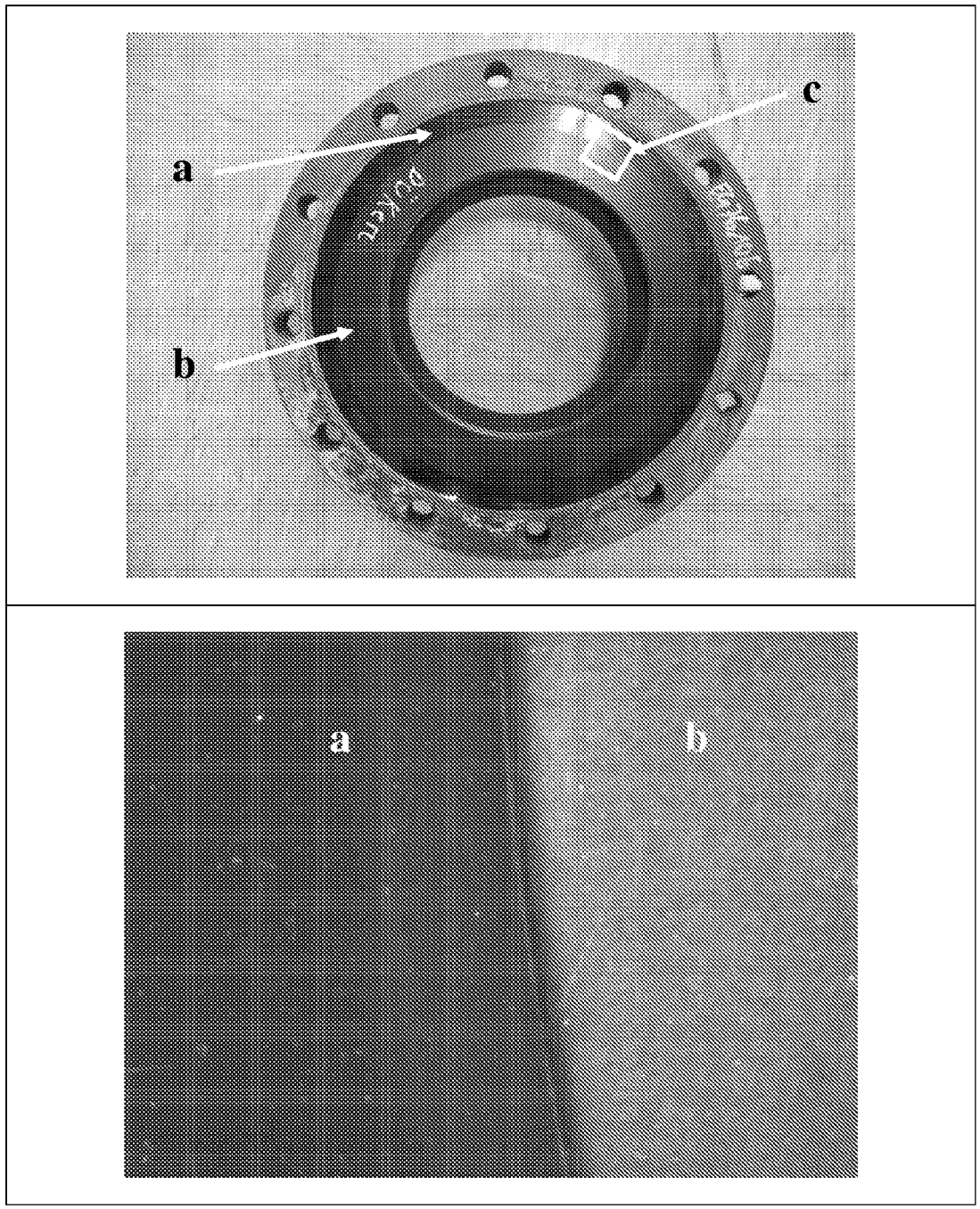

USE OF COMPOSITIONS CONTAINING SILICON FOR IMPROVING THE CORROSION RESISTANCE OF VESSELS

CROSS-REFERENCE TO RELATED APPLICATIONS

The present patent application is a U.S. national stage application under 35 U.S.C. §371 of International Application No. PCT/EP2008/062845 filed Sep. 25, 2008, which claims the benefit of the U.S. Provisional Patent Application No. 60/976,845 filed on Oct. 2, 2007, the content of each of these applications which is incorporated herein by reference.

The present invention relates to the use of a composition containing silicon (Si) and oxygen in equipments. More specifically, the composition is used in an equipment intended to be in contact with a mixture containing a chlorohydrin, hydrogen chloride and water.

Chlorohydrins are reaction intermediates in the manufacture of epoxides. Dichloropropanol, for example, is a reaction intermediate in the manufacture of epichlorohydrin and epoxy resins (Kirk-Othmer Encyclopedia of Chemical Technology, Fourth Edition, 1992, Vol. 2, page 156, John Wiley & sons Inc.).

According to known processes, dichloropropanol can be obtained in particular by hypochlorination of allyl chloride, by chlorination of allyl alcohol or by hydrochlorination of glycerol. The latter process exhibits the advantage that the dichloropropanol can be obtained starting from fossil raw materials or renewable raw materials and it is known that petrochemical natural resources, from which fossil materials originate, for example oil, natural gas or coal, available on the earth are limited. The latter process generates mixtures of chlorhydrin, water and hydrogen chloride.

International applications WO 2005/054167 and WO 2006/100317 of SOLVAY SA and WO 2006/020234 describe a process for manufacturing dichloropropanol by reaction between glycerol and hydrogen chloride. Several corrosion resistant materials are mentioned for the fabrication of equipment used in the process. However, some of those materials have a resistance to corrosion by the reaction mixture at the process conditions which is not optimal. This would result in a risk of contamination of the process product by equipment materials components and request therefore replacement of the equipment susceptible of negatively affect the economy of the process.

The invention aims to solve this problem.

In a first embodiment, the invention therefore relates to the use of a composition comprising silicon, oxygen and calcium, wherein silicon is present in an amount higher than or equal to 235 g of Si per kg of composition and calcium is present in an amount lower than or equal to 25 g of Ca per kg of composition, as a material for coating an equipment or as a constituent material of equipment, intended to be in contact with a mixture containing a chlorohydrin, hydrogen chloride and water.

In a second embodiment, the invention therefore relates to the use of a composition comprising silicon, oxygen and potassium, wherein, silicon is present in an amount higher than or equal to 235 g of Si per kg of composition and potassium is present in an amount higher than or equal to 4 g of K per kg of composition, as a material for coating an equipment or as a constituent material of equipment, intended to be in contact with a mixture containing a chlorohydrin, hydrogen chloride and water.

In a third embodiment, the invention therefore relates to the use of a composition comprising silicon, oxygen and titanium, wherein silicon is present in an amount higher than or equal to 235 g of Si per kg of composition and titanium is present in an amount lower than or equal to 10 g of Ti per kg of composition, as a material for coating an equipment or as a constituent material of equipment, intended to be in contact with a mixture containing a chlorohydrin, hydrogen chloride and water.

In the use according to the invention, the composition may be an organic composition or an inorganic composition. The composition is preferably an inorganic composition.

In the use according to the invention, the composition may be in any physical state. It is preferably in a glassy state. By glassy state one intends to denote a rigid uncrystallized state. Some enamels are examples of inorganic compositions in the glassy state. By enamel, one intends to denote a fused vitreous superficial coating containing mainly silicon oxide.

In the use according to the invention, the composition is preferably an enamel.

One of the essential characteristics of the first embodiment of the invention resides in the low content of calcium in the composition which renders it less prone to corrosion by the mixture containing a chlorohydrin, hydrogen chloride and water.

One of the essential characteristics of the second embodiment of the invention resides in the high content of potassium in the composition which renders it less prone to corrosion by the mixture containing a chlorohydrin, hydrogen chloride and water.

One of the essential characteristics of the third embodiment of the invention resides in the low content of titanium in the composition which renders it less prone to corrosion by the mixture containing a chlorohydrin, hydrogen chloride and water.

It has indeed surprisingly been found that the above compositions are very resistant to the corrosion by mixtures containing a chlorohydrin, water and hydrogen chloride, which corrosiveness has surprisingly been found higher than that of mixture containing only water and hydrogen chloride.

The advantages of the use according to the invention are among others:
- A decrease of the frequency of replacement of equipment
- A lowering of the risks linked to equipment breakage and leak
- A lessening of the contamination of process products by the equipment material components.

In the three embodiments of the use according to the invention, the silicon content of the composition, per kg of composition, is frequently higher than or equal to 275 g of Si, often higher than or equal to 300 g of Si and in many cases higher than or equal to 320 g of Si. That silicon content is generally lower than or equal to 400 g of Si, frequently lower than or equal to 350 g of Si and often lower than or equal to 335 g of Si.

In the first embodiment of the use according to the invention, the calcium content of the composition, per kg of composition, is frequently lower than or equal to 20 g of Ca and often lower than or equal to 15 g of Ca. That content is frequently higher than or equal to 0.1 g of Ca, often higher than or equal to 1 g of Ca, in many cases higher than or equal to 5 g of Ca and in particular higher than or equal to 10 g of Ca.

In a first variant of the first embodiment of the use according to the invention, the composition may in addition comprise potassium. The potassium content of the composition, per kg of composition, is generally higher than or equal to 0.1 g of K, often higher than or equal to 1 g of K, in many cases higher than or equal to 4 g of K and frequently higher than or equal to 10 g of K. That potassium content is usually lower than or equal to 60 g of K, often lower than or equal to 50 g of K, in many cases lower than or equal to 30 g of K and frequently lower than or equal to 25 g of K.

In a second variant of the first embodiment of the use according to the invention, the composition may in addition comprise titanium. The titanium content of the composition, per kg of composition, is generally higher than or equal to 0.1 g of Ti, often higher than or equal to 1 g of Ti, in many cases higher than or equal to 4 g of Ti and frequently higher than or equal to 6 g of Ti. That titanium content is usually lower than or equal to 60 g of Ti, generally lower than or equal to 40 g of Ti, often lower than or equal to 20 g of Ti, in many cases lower than or equal to 10 g of Ti and frequently lower than or equal to 8 g of Ti.

In a third variant of the first embodiment of the use according to the invention, the composition often contains, per kg of composition, silicon in an amount higher than or equal to 300 g of Si, calcium in an amount lower than or equal to 25 g of Ca, and potassium in an amount higher than or equal to 4 g of K.

In a fourth variant of the first embodiment of the use according to the invention, the composition frequently contains, per kg of composition, silicon in an amount higher than or equal to 300 g of Si, calcium in an amount lower than or equal to 25 g of Ca and titanium in an amount lower than or equal to 10 g of Ti.

In a fifth variant of the first embodiment of the use according to the invention, the composition often contains, per kg of composition, silicon in an amount higher than or equal to 300 g of Si, calcium in an amount lower than or equal to 25 g of Ca, potassium in an amount higher than or equal to 4 g of K and titanium in an amount lower than or equal to 10 g of Ti.

In the second embodiment of the use according to the invention, the potassium content of the composition, per kg of composition, is often higher than or equal to 6 g of K, in many cases higher than or equal to 8 g of K and frequently higher than or equal to 12 g of K. That potassium content is usually lower than or equal to 60 g of K, often lower than or equal to 50 g of K, in many cases lower than or equal to 30 g of K and frequently lower than or equal to 25 g of K.

In a first variant of the second embodiment of the use according to the invention, the composition may in addition comprise calcium. The calcium content of the composition, per kg of composition, is usually lower than or equal to 50 g of Ca, often lower than or equal to 25 g of Ca and in many cases lower than or equal to 15 g of Ca. That content is frequently higher than or equal to 0.1 g of Ca, often higher than or equal to 1 g of Ca, in many cases higher than or equal to 5 g of Ca and in particular higher than or equal to 10 g of Ca.

In a second variant of the second embodiment of the use according to the invention, the composition may in addition comprise titanium. The titanium content of the composition, per kg of composition, is generally higher than or equal to 0.1 g of Ti, often higher than or equal to 1 g of Ti, in many cases higher than or equal to 4 g of Ti and frequently higher than or equal to 6 g of Ti. That titanium content is usually lower than or equal to 60 g of Ti, generally lower than or equal to 40 g of Ti, often lower than or equal to 20 g of Ti, in many cases lower than or equal to 10 g of Ti and frequently lower than or equal to 8 g of Ti.

In a third variant of the second embodiment of the use according to the invention which is identical to the third variant of the first embodiment, the composition often contains, per kg of composition, silicon in an amount higher than or equal to 300 g of Si, potassium in an amount higher than or equal to 4 g of K and calcium in an amount lower than or equal to 25 g of Ca.

In a fourth variant of the second embodiment of the use according to the invention, the composition frequently contains, per kg of composition, silicon in an amount higher than or equal to 300 g of Si, potassium in an amount higher than or equal to 4 g of K and titanium in an amount lower than or equal to 10 g of Ti.

In a fifth variant of the second embodiment of the use according to the invention which is identical to the fifth variant of the first embodiment, the composition often contains, per kg of composition, silicon in an amount higher than or equal to 300 g of Si, potassium in an amount higher than or equal to 4 g of K, calcium in an amount lower than or equal to 25 g of Ca, and titanium in an amount lower than or equal to 10 g of Ti.

In the third embodiment of the use according to the invention, the titanium content of the composition, per kg of composition, is generally higher than or equal to 0.1 g of Ti, often higher than or equal to 1 g of Ti, in many cases higher than or equal to 4 g of Ti and frequently higher than or equal to 5 g of Ti. That titanium content is often lower than or equal to 8 g of Ti and in many cases lower than or equal to 6 g of Ti.

In a first variant of the third embodiment of the use according to the invention, the composition may in addition comprise potassium. The potassium content of the composition, per kg of composition, is generally higher than or equal to 0.1 g of K, often higher than or equal to 1 g of K, in many cases higher than or equal to 4 g of K and frequently higher than or equal to 10 g of K. That potassium content is usually lower than or equal to 60 g of K, often lower than or equal to 50 g of K, in many cases lower than or equal to 30 g of K and frequently lower than or equal to 25 g of K.

In a second variant of the third embodiment of the use according to the invention, the composition may in addition comprise calcium. The calcium content of the composition, per kg of composition, is usually lower than or equal to 50 g of Ca, often lower than or equal to 25 g of Ca and in many cases lower than or equal to 15 g of Ca. That content is frequently higher than or equal to 0.1 g of Ca, often lower than or equal to 1 g of Ca, in many cases higher than or equal to 5 g of Ca and in particular higher than or equal to 10 g of Ca.

In a third variant of the third embodiment of the use according to the invention which is identical to the fourth variant of the second embodiment, the composition often contains, per kg of composition, silicon in an amount higher than or equal to 300 g of Si, titanium in an amount lower than or equal to 10 g of Ti and potassium in an amount higher than or equal to 4 g of K.

In a fourth variant of the third embodiment of the use according to the invention which is identical to the fourth variant of the first embodiment, the composition frequently contains, per kg of composition, silicon in an amount higher than or equal to 300 g of Si, titanium in an amount lower than or equal to 10 g of Ti and calcium in an amount lower than or equal to 25 g of Ca.

In a fifth variant of the third embodiment of the use according to the invention which is identical to the fifth variant of the first embodiment, the composition often contains, per kg of composition, silicon in an amount higher than or equal to 300 g of Si, titanium in an amount lower than or equal to 10 g of Ti, potassium in an amount higher than or equal to 4 g of K and calcium in an amount lower than or equal to 25 g of Ca.

In the first three embodiments of the use according to the invention, the composition may in addition comprise at least one of the elements selected from sodium, aluminium, magnesium, cobalt, zirconium, barium, iron, strontium and zinc.

The content of sodium, per kg of composition, is usually higher than or equal to 70 g of Na, often higher than or equal to 80 g of Na and frequently higher than or equal to 90 g of Na. That sodium content is generally lower than or equal to 150 g of Na, in many cases lower than or equal to 130 g of Na and frequently lower than or equal to 110 g of Na.

The content of aluminium, per kg of composition, is usually higher than or equal to 0.1 g of Al, often higher than or equal to 1 g of Al and frequently higher than or equal to 5 g of Al. That aluminium content is generally lower than or equal to 15 g of Al, in many cases lower than or equal to 10 g of Al and frequently lower than or equal to 8 g of Al.

The content of magnesium, per kg of composition, is usually higher than or equal to 0.1 g of Mg, often higher than or equal to 1 g of Mg and frequently higher than or equal to 5 g of Mg. That magnesium content is generally lower than or equal to 10 g of Mg, in many cases lower than or equal to 8 g of Mg and frequently lower than or equal to 6 g of Mg.

The content of cobalt, per kg of composition, is usually higher than or equal to 0.1 g of Co, often higher than or equal to 1 g of Co and frequently higher than or equal to 5 g of Co. That cobalt content is generally lower than or equal to 10 g of Co and in many cases lower than or equal to 8 g of Co.

The content of zirconium, per kg of composition, is usually higher than or equal to 25 g of Zr, often higher than or equal to 35 g of Zr and frequently higher than or equal to 50 g of Zr. That zirconium content is generally lower than or equal to 70 g of Zr and in many cases lower than or equal to 60 g of Zr.

The content of barium, per kg of composition, is usually higher than or equal to 0.1 g of Ba, often higher than or equal to 1 g of Ba and frequently higher than or equal to 5 g of Ba. That barium content is generally lower than or equal to 30 g of Ba, in many cases lower than or equal to 20 g of Ba and frequently lower than or equal to 10 g of Ba.

The content of iron per kg of composition, is usually higher than or equal to 0.1 g of Fe, often higher than or equal to 1 g of Fe and frequently higher than or equal to 5 g of Fe. That iron content is generally lower than or equal to 10 g of Fe and in many cases lower than or equal to 8 g of Fe.

The content of strontium, per kg of composition, is usually higher than or equal to 0.1 g of Sr, often higher than or equal to 1 g of Sr and frequently higher than or equal to 5 g of Sr. That strontium content is generally lower than or equal to 15 g of Sr, in many cases lower than or equal to 10 g of Sr and frequently lower than or equal to 8 g of Sr.

The content of zinc, per kg of composition, is usually higher than or equal to 0.1 g of Zn, often higher than or equal to 1 g of Zn and frequently higher than or equal to 5 g of Zn. That zinc content is generally lower than or equal to 15 g of Zn, in many cases lower than or equal to 10 g of Zn and frequently lower than or equal to 8 g of Zn.

In the first three embodiments of the use according to the invention, the composition may in addition comprise at least one of the elements selected from chromium, copper, manganese, nickel, phosphorus and vanadium, in traces concentration, i.e., lower than or equal to 0.1 g of element.

In the first three embodiments of the use according to the invention, the ratio between potassium and calcium expressed in equivalent of electrical charges, i.e. number of moles of K divided by 2 times the number of moles of Ca, is usually higher than or equal to 0.05, often higher than or equal to 0.1, frequently higher than or equal to 0.2, in many case higher than or equal to 0.4 and in particular higher than or equal to 0.6. That ratio is generally lower than or equal to 2, frequently lower than or equal to 1 and often lower than or equal to 0.8.

In the first three embodiments of the use according to the invention, the ratio between the alkaline metals and the alkaline-earth metals expressed in equivalent of electrical charges, i.e. the sum of the number of moles of alkali metals divided by 2 times the sum of the number of moles of the alkaline-earth metals, is usually higher than or equal to 2.8, often higher than or equal to 3.0, frequently higher than or equal to 3.2 and in many case higher than or equal to 3.4. That ratio is generally lower than or equal to 4, frequently lower than or equal to 3.8 and often lower than or equal to 3.7.

In the composition used in the invention, those elements are generally present in combination with the oxygen present in the composition, preferably in the form of oxides. These oxides may be hydrated to a greater or lesser extent. The oxides can be single oxides or mixed oxides. Single oxides are for example, alkaline metal oxides such as $Li_2O$, $Na_2O$, $K_2O$, alkaline-earth metal oxides, like MgO, CaO, SrO, BaO, oxides of Family Ma of the Periodic Table of the Elements like $B_2O_3$, $Al_2O_3$, oxides of Families IVa and Va of the Periodic Table of the Elements like PbO an $Sb_2O_3$, and oxides from Families IIb to VIIb and VIII of the Periodic Table of the Elements like ZnO, CoO, $ZrO_2$, $TiO_2$ and $CeO_2$. An example of a mixed oxide is $KNa_2O$. These elements may also be present as fluorides like for instance $SiF_4$, $Na_2F_2$ and $CaF_2$.

In the composition used in the invention, those elements are preferably present in combination with the oxygen, preferably in the form of oxides.

One particularly preferred composition in the use according to the invention comprises oxygen and per kg of composition, 100 g of Na, 315 g of Si, 8.1 g of K, 13 g of Ca, 7.6 g of Co, 63 g of Zr and 22 g of Ba. The composition contains, in addition, aluminium, magnesium, titanium, iron, strontium and zinc, each in an amount less than 5 g/kg of composition. That composition has been obtained by analysis of the outer layer of an enamelled steel bar sample provided by the firm DE DIETRICH.

Another particularly preferred composition in the use according to the invention comprises oxygen and per kg of composition, 78 g of Na, 9.6 g of Al, 330 g of Si, 19 g of K, 14 g of Ca, 6.2 g of Co, 34 g of Zr, 6.3 g of Ba, 5.4 g of Fe, 12 g of Sr and 11 g of Zn. The composition contains, in addition, magnesium and titanium, each in an amount less than 5 g/kg of composition. That composition has been obtained by analysis of the outer layer of an enamelled steel bar sample provided by the firm PFAUDLER.

Another particularly preferred composition in the use according to the invention comprises oxygen and per kg of composition, 82 g of Na, 12 g of Al, 340 g of Si, 14 g of K, 15 g of Ca, 5.4 g of Ti, 7.8 g of Co, 22 g of Zr and 4.3 g of Sr. The composition contains, in addition, barium, iron and zinc, each in an amount less than 5 g/kg. That composition has been obtained by analysis of the outer layer of an enamelled steel bar sample provided by the firm THALE.

The values of the contents of the elements in the compositions are given with a relative error of ±5%.

It has been found that such compositions have an excellent resistance to corrosion by the mixture containing a chlorohydrin, hydrogen chloride and water. In particular, when used as a coating material, they make it possible to greatly reduce the cost of equipment resistant to corrosion by the aforementioned mixture.

The use of the composition according to the invention as a component of a material for coating equipment or as a constituent material of equipment, depends on the numerous factors linked to the usage conditions of the equipment (temperature and pressure), to the nature of the chlorohydrin (monochlorohydrin, dichlorohydrin, chemical nature), to the presence of another compound such as a carboxylic acid for example, to the hydrogen chloride, to the composition of the mixture containing the chlorohydrin, hydrogen chloride and water, to the nature and to the implementation method of the equipment and to the features of the equipment to be protected.

The factors linked to the hydrogen chloride are, for example, its chemical purity and its physical state (dissolved, dispersed, gaseous).

The factors linked to the equipment are, for example, the shape, size, complexity, access to the surfaces, easiness to control the surface characteristics (like the temperature) of the equipment to be protected.

In the use of the composition according to the invention, the contact with the mixture containing a chlorohydrin, hydrogen chloride and water, is generally carried out at a temperature greater than or equal to 60° C., preferably greater than or equal to 90° C., more preferably greater than or equal to 110° C. and most particularly preferably greater than or equal to 125° C. This temperature is generally less than or equal to 200° C., preferably less than or equal to 180° C., more preferably less than or equal to 160° C. and most particularly preferably less than or equal to 145° C.

In the use of the composition according to the invention, the contact with the mixture containing a chlorohydrin, hydrogen chloride and water, is generally carried out at a pressure greater than or equal to 0.04 bar absolute, preferably greater than or equal to 0.2 bar absolute, more preferably greater than or equal to 0.5 bar absolute and most particularly preferably greater than or equal to 1.1 bar absolute. This pressure is generally less than or equal to 20 bar absolute, preferably less than or equal to 15 bar absolute, more preferably less than or equal to 5 bar absolute and most particularly preferably less than or equal to 1.3 bar absolute.

The chlorohydrin may be present as is, that is to say not combined chemically, and/or in the form of esters with a carboxylic acid optionally present in the mixture of hydrogen chloride, water and chlorohydrin.

The content of chlorohydrin (as is and/or in the form of esters) of the mixture in the use according to the invention, expressed in moles of chlorohydrin per kg of mixture, is generally greater than or equal to 0.1, often greater than or equal to 0.5, frequently greater than or equal to 1.0 more, frequently greater than or equal to 2.0 and more specifically greater than or equal to 3.5. This chlorohydrin content is generally less than or equal to 8 mol/kg, often less than or equal to 7 mol/kg, frequently less than or equal to 5 mol/kg and more specifically less than or equal to 4.0 mol/kg.

The chlorohydrin is preferably chosen from dichloropropanol, monochloropropanediol, and mixtures thereof.

In this case, the content of chlorohydrin (as is and/or in the form of esters) of the mixture in the use according to the invention, expressed in g of chlorohydrin per kg of mixture, is generally greater than or equal to 50, often greater than or equal to 100, frequently greater than or equal to 200 and more specifically greater than or equal to 500. This chlorohydrin content is generally less than or equal to 994 g/kg, often less than or equal to 950 g/kg, frequently less than or equal to 900 g/kg and more specifically less than or equal to 800 g/kg.

The hydrogen chloride content of the mixture in the use according to the invention is generally greater than or equal to 1 g per kg of mixture, often greater than or equal to 2 g/kg, frequently greater than or equal to 5 g/kg and more specifically greater than or equal to 7 g/kg. This hydrogen chloride content is commonly less than or equal to 750 g/kg, in many cases less than or equal to 600 g/kg, usually less than or equal to 400 g/kg, generally less than or equal to 250 g/kg, often less than or equal to 200 g/kg, frequently less than or equal to 100 g/kg, in particular less than or equal to 50 g/kg and more specifically less than or equal to 20 g/kg.

The water content of the mixture in the use according to the invention is generally greater than or equal to 5 g per kg of mixture, often greater than or equal to 10 g/kg, frequently greater than or equal to 20 g/kg and more specifically greater than or equal to 50 g/kg. This water content is generally less than or equal to 900 g/kg, usually less than or equal to 800 g/kg, commonly less than or equal to 600 g/kg, in many cases less than or equal to 400 g/kg, often less than or equal to 200 g/kg, frequently less than or equal to 150 g/kg and more specifically less than or equal to 100 g/kg.

Other compounds may be present in the mixture in the use according to the invention. These compounds may, for example, come from the manufacture of the chlorohydrin and/or hydrogen chloride and/or originate from water.

The mixture containing the chlorohydrin, hydrogen chloride and water may be obtained in any way, for example by reacting a polyhydroxylated aliphatic hydrocarbon, an ester of a polyhydroxylated aliphatic hydrocarbon or a mixture of the two, with a chlorinating agent that contains hydrogen chloride, or during the hypochlorination reaction of a chloroolefin, or by chlorination of a hydroxylated olefin. The process for obtaining the mixture containing the chlorohydrin, hydrogen chloride and water, may carried out in any mode, like for instance, the continuous mode, the batch mode and the fed-batch mode.

The term "olefin" is used here to describe a compound containing at least one carbon-carbon double bond. In general the compound may contain atoms other than carbon atoms, such as hydrogen atoms and halogens. The preferred olefins are ethylene, propylene, allyl chloride and mixtures of at least two thereof.

The term "polyhydroxylated aliphatic hydrocarbon" refers to a hydrocarbon which contains at least two hydroxyl groups attached to two different saturated carbon atoms. The polyhydroxylated aliphatic hydrocarbon may contain, but is not limited to, from 2 to 60 carbon atoms.

Each of the carbons of a polyhydroxylated aliphatic hydrocarbon carrying the hydroxyl (OH) functional group may not possess more than one OH group and must be of sp3 hybridization. The carbon atom carrying the OH group may be primary, secondary or tertiary. The polyhydroxylated aliphatic hydrocarbon used in the present invention must contain at least two sp3-hybridized carbon atoms carrying an OH group. The polyhydroxylated aliphatic hydrocarbon includes any hydrocarbon containing a vicinal diol (1,2-diol) or a vicinal triol (1,2,3-triol), including higher orders of these repeating units, which are vicinal or contiguous. The definition of the polyhydroxylated aliphatic hydrocarbon also includes, for example, one or more 1,3-, 1,4-, 1,5- and 1,6-diol functional groups. The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic moieties or heteroatoms including, for example, heteroatoms of halogen, sulphur, phosphorus, nitrogen, oxygen, silicon and boron type, and mixtures thereof.

Polyhydroxylated aliphatic hydrocarbons which can be used in the present invention include, for example, 1,2-ethanediol (ethylene glycol), 1,2-propanediol (propylene glycol), 1,3-propanediol, 1-chloro-2,3-propanediol (chloropropanediol), 2-chloro-1,3-propanediol (chloropropanediol), 1,4-butanediol, 1,5-pentanediol, cyclohexanediols, 1,2-butanediol, 1,2-cyclohexanedimethanol, 1,2,3-propanetriol (also known as glycerol or glycerin), and mixtures thereof. With preference the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two thereof. More preferably the polyhydroxylated aliphatic hydrocarbon used in the present invention includes, for example, 1,2-ethanediol, 1,2-propanediol, chloropropanediol and 1,2,3-propanetriol and mixtures of at least two thereof. 1,2,3-Propanetriol, or glycerol, is the most preferred.

The esters of polyhydroxylated aliphatic hydrocarbon may be present in the polyhydroxylated aliphatic hydrocarbon and/or may be produced in the process of preparing the chlorohydrin and/or may be prepared prior to the process of preparing the chlorohydrin. Examples of esters of polyhydroxylated aliphatic hydrocarbon include ethylene glycol monoacetate, propanediol monoacetates, glycerol monoacetates, glycerol monostearates, glycerol diacetates and mixtures thereof.

In the process according to the invention, the esters of the polyhydroxylated aliphatic hydrocarbon may originate from the reaction of the polyhydroxylated aliphatic hydrocarbon with an organic acid, before, during or within the steps which follow the reaction with the chlorinating agent.

The term "chlorohydrin" is used here to describe a compound containing at least one hydroxyl group and at least one chlorine atom which are attached to different saturated carbon atoms. A chlorohydrin which contains at least two hydroxyl groups is also a polyhydroxylated aliphatic hydrocarbon. Hence the starting material and the product of the reaction may each be chlorohydrins. In that case the "product" chlorohydrin is more chlorinated than the starting chlorohydrin; in other words, it has more chlorine atoms and fewer hydroxyl groups than the starting chlorohydrin. Preferred chlorohydrins are chloroethanol, chloropropanol, chloropropanediol, dichloropropanol and mixtures of at least two thereof. Dichloropropanol is particularly preferred. Chlorohydrins which are more particularly preferred are 2-chloroethanol, 1-chloropropan-2-ol, 2-chloropropan-1-ol, 1-chloropropane-2,3-diol, 2-chloropropane-1,3-diol, 1,3-dichloropropan-2-ol, 2,3-dichloropropan-1-ol and mixtures of at least two thereof.

The polyhydroxylated aliphatic hydrocarbon is preferably glycerol. The chloroolefin is preferably allyl chloride. The hydroxylated olefin is preferably allyl alcohol. The chlorohydrin is preferably chosen from monochloropropanediol, dichloropropanol and mixtures thereof.

In the use according to the invention, the polyhydroxylated aliphatic hydrocarbon may be obtained starting from fossil raw materials or starting from renewable raw materials, preferably starting from renewable raw materials, as described in WO 2005/054167 of SOLVAY SA, the content of which is incorporated herein by reference, and especially the passages from page 1, line 26, to page 4, line 2, and as described in WO 2006/100312 of SOLVAY SA, the content of which is incorporated herein by reference, and especially the passages from page 3, line 29, to page 5, line 24, and as described in PCT/EP/of SOLVAY SA, the content of which is incorporated herein by reference, and especially the passages at page 10, lines 16 to 23, and at page 11, lines 4 to 25.

In the use according to the invention, the polyhydroxylated aliphatic hydrocarbon may have an alkali metal and/or alkaline earth metal content as described in WO 2006/100315 of SOLVAY SA, the content of which is incorporated herein by reference, and especially the passages from page 7, line 11, to page 9, line 10.

In the use according to the invention, the polyhydroxylated aliphatic hydrocarbon may contain elements other than alkali metals and alkaline earth metals as described in WO 2006/100319 of SOLVAY SA, the content of which is incorporated herein by reference, especially the passages from page 2, line 3 to 8, and from page 6, line 20, to page 9, line 14.

In the use according to the invention, the polyhydroxylated aliphatic hydrocarbon contains generally an amount of heavy compounds other glycerol and whose boiling temperature under a pressure of 1 bar absolute is at least 15° C. greater than the boiling temperature of dichloropropanol as described in WO 2006/100316 of SOLVAY SA the content of which is incorporated herein by reference, especially the passages from page 15, line 32, to page 17, line 33.

In the use according to the invention, the polyhydroxylated aliphatic hydrocarbon may contain alkylated ethers of the polyhydroxylated hydrocarbon such as described in WO 2007/144335 of SOLVAY SA the content of which is incorporated herein by reference, especially the passages from page 1, line 23, to page 3, line 25.

In the use according to the invention, the polyhydroxylated aliphatic hydrocarbon may contain diols, monoalcohols, ketones, aldehydes, alkyl esters of fatty acids, glycerol esters, carboxylic acids and salt such as described in PCT/EP2008/057876 of SOLVAY SA the content of which is incorporated herein by reference, especially the passages from page 1, line 30, to page 3, line 21, and from page 4, line 3, to page 6, line 2.

In the use according to the invention, the polyhydroxylated aliphatic hydrocarbon may contain nitrogen containing compounds as described in FR 07/59891 of SOLVAY SA the content of which is incorporated herein by reference, especially the passages from page 1, line 28, to page 3, line 20.

In the use according to the invention, the polyhydroxylated aliphatic hydrocarbon may contain glycerol oligomers as described in FR 08/52206 of SOLVAY SA the content of which is incorporated herein by reference, especially the passages from page 1, line 19, to page 4, line 18.

In the application according to the invention, the mixture containing the chlorohydrin, hydrogen chloride and water is preferably obtained during the reaction between a polyhydroxylated aliphatic hydrocarbon, an ester of a polyhydroxylated aliphatic hydrocarbon or a mixture of the two, with a chlorinating agent that contains hydrogen chloride.

In the reaction for obtaining the mixture containing chlorohydrin, hydrogen chloride and water, the hydrogen chloride may be a gas, optionally anhydrous, or an aqueous solution of hydrogen chloride or a mixture thereof. The hydrogen chloride is often a gas or a mixture of a gas and an aqueous solution of hydrogen chloride. The hydrogen chloride may at least partially be obtained from processes such as described in WO 2005/054167 of SOLVAY SA, the content of which is incorporated herein by reference, especially the passages from page 4, line 32, to page 5, line 35, such as described in WO 2006/106153 of SOLVAY SA, the content of which is incorporated herein by reference, especially the passages from page 2, line 10, to page 3, line 20, and from page 11, line 1 to page 18, line 29, and such as described in WO 2007/144335 of SOLVAY SA, the content of which is incorporated herein by reference, especially the passages from page 12, line 14, to page 14, line 21.

In the reaction for obtaining the mixture containing chlorohydrin, hydrogen chloride and water, the hydrogen chloride may be purified such as described in FR 08/56138 of SOLVAY SA, the content of which is incorporated herein by reference, especially the passages from page 2, line 33, to page 16, line 21.

The reaction for obtaining the mixture containing chlorohydrin, hydrogen chloride and water may be carried out in a reaction medium such described in WO 2006/106154 of SOLVAY SA, the content of which is incorporated herein by reference, especially the passages from page 14, line 15, to page 17, line 10.

The reaction for obtaining the mixture containing chlorohydrin, hydrogen chloride and water may be carried out in the presence of a catalyst such described in WO 2005/054167 of SOLVAY SA, the content of which is incorporated herein by reference, especially the passages from page 6, line 24, to page 8, line 15, and such described in WO 2006/020234, the content of which is incorporated herein by reference, especially the passages from page 12, line 20, to page 18, line 3, and in FR 07/59891, the content of which is incorporated herein by reference, especially the passage at page 8, lines 18 to 21.

The reaction for obtaining the mixture containing chlorohydrin, hydrogen chloride and water may be carried out for a catalyst concentration, at a temperature, at a pressure and at a residence time such described in WO 2005/054167 of SOLVAY SA, the content of which is incorporated herein by reference, especially the passages from page 8, line 1, to page 10, line 10.

The reaction for obtaining the mixture containing chlorohydrin, hydrogen chloride and water may be carried out such described in WO 2007/054505 of SOLVAY SA, the content of which is incorporated herein by reference, especially the passages from page 1, line 24 to page 6, line 18.

The reaction for obtaining the mixture containing chlorohydrin, hydrogen chloride and water may be carried out in the presence of a solvent such described in WO 2005/054167 of SOLVAY SA, the content of which is incorporated herein by reference, especially the passages at page 11, line 12 to 36.

The reaction for obtaining the mixture containing chlorohydrin, hydrogen chloride and water may be carried out in the presence of a liquid phase comprising heavy compounds other than glycerol such described in WO 2006/100316 of SOLVAY SA, the content of which is incorporated herein by reference, especially the passages at page 2, lines 18 to 25 and from page 15, line 32, to page 17, line 33.

The reaction for obtaining the mixture containing chlorohydrin, hydrogen chloride and water may be carried out under stirring with a stirring system such described in PCT/EP2008/056688 of SOLVAY SA, the content of which is incorporated herein by reference, especially the passages from page 1, line 30, to page 2, line 33, and from page 6, line 22, to page 14, line 31.

The reaction for obtaining the mixture containing chlorohydrin, hydrogen chloride and water may be carried out in a liquid reaction medium such described in WO 2006/106154 of SOLVAY SA, the content of which is incorporated herein by reference, especially the passages from page 1, line 29, to page 2, line 6, and from page 14, line 15, to page 17, line 10.

The reaction for obtaining the mixture containing chlorohydrin, hydrogen chloride and water may be carried out in a reactor the feeding of which is described in PCT/EP2008/052711 of SOLVAY SA, the content of which is incorporated herein by reference, especially the passages from page 1, line 29, to page 4, line 27, and from page 5, line 34, to page 9, line 17.

In the process for obtaining the mixture containing chlorohydrin, hydrogen chloride and water, a separation of the chlorohydrin from the other compounds of the reaction mixture may be carried out such described in WO 2005/054167 of SOLVAY SA, the content of which is incorporated herein by reference, especially the passages from page 12, line 1, to page 17, line 20.

In the process for obtaining the mixture containing chlorohydrin, hydrogen chloride and water, a separation of the chlorohydrin from the other compounds of the reaction mixture may be carried out such described in WO 2006/100312 of SOLVAY SA, the content of which is incorporated herein by reference, especially the passages at page 2, lines 3 to 10, at page 20, line 28 to page 28, line 20.

In the process for obtaining the mixture containing chlorohydrin, hydrogen chloride and water, a separation of the chlorohydrin from the other compounds of the reaction mixture may be carried out according to methods such described in WO 2006/100313 of SOLVAY SA, the content of which is incorporated herein by reference, especially the passages at page 2, lines 1 to 23, and from page 21, line 7, to page 25, line 25.

In the process for obtaining the mixture containing chlorohydrin, hydrogen chloride and water, a separation of the chlorohydrin from the other compounds of the reaction mixture may be carried out according to methods such described in WO 2006/100314 of SOLVAY SA, the content of which is incorporated herein by reference, especially the passages at page 2, lines 6 to page 3, line 4, and from page 18, line 33, to page 22, line 29.

In the process for obtaining the mixture containing chlorohydrin, hydrogen chloride and water, a separation of the chlorohydrin from the other compounds of the reaction mixture may be carried out according to methods such described in WO 2006/100320 of SOLVAY SA, the content of which is incorporated herein by reference, especially the passages from page 1, line 30, to page 2, line 23 and from page 6, line 25, to page 10, line 28.

In the process for obtaining the mixture containing chlorohydrin, hydrogen chloride and water, a separation of the chlorohydrin from the other compounds of the reaction mixture may be carried out according to methods such described in WO 2006/100315 of SOLVAY SA, the content of which is incorporated herein by reference, especially the passages at page 2, lines 3 to 29, and from page 23, line 3, to page 24, line 13.

In the process for obtaining the mixture containing chlorohydrin, hydrogen chloride and water, a separation of the chlorohydrin from the other compounds of the reaction mixture may be carried out according to methods such described in PCT/EP2008/052972 of SOLVAY SA, the content of which is incorporated herein by reference, especially the passages from page 1, line 31, to page 27, line 25.

In the process for obtaining the mixture containing chlorohydrin, hydrogen chloride and water, when the chlorohydrin is dichloropropanol, the dichloropropanol is generally obtained as a mixture of 1,3-dichloropropan-2-ol and 2,3-dichloropropan-1-ol isomers such described in WO 2006/100319 of SOLVAY SA, the content of which is incorporated herein by reference, especially the passages from page 23, line 34, to page 24, line 29.

In the process for obtaining the mixture containing chlorohydrin, hydrogen chloride and water, the chlorohydrin may contain halogenated ketones such described in WO 2006/100311 of SOLVAY SA, the content of which is incorporated herein by reference, especially the passages at page 2, lines 22 to 34, and from page 22, line 8, to page 23, line 35.

In the process for obtaining the mixture containing chlorohydrin, hydrogen chloride and water, water which have been in contact with equipment walls may be treated such described in FR 08/56059 of SOLVAY SA, the content of which is incorporated herein by reference, especially the passages from page 1, line 7, to page 16, line 34.

When the mixture containing the chlorohydrin, hydrogen chloride and water is obtained during the reaction between a polyhydroxylated aliphatic hydrocarbon, an ester of a polyhydroxylated aliphatic hydrocarbon or a mixture of the two, with a chlorinating agent that contains hydrogen chloride, it is possible to find, among the compounds which may come from the chlorohydrin manufacturing process, polyhydroxylated aliphatic hydrocarbons, esters of a polyhydroxylated aliphatic hydrocarbon, chlorohydrin esters, carboxylic acids, oligomers of the polyhydroxylated aliphatic hydrocarbon that are partially chlorinated and/or esterified.

In the use according to the invention, the mixture containing the chlorohydrin, hydrogen chloride and water, is preferably obtained by reaction glycerol, glycerol esters, or a mixture thereof, with a chlorinating agent that contains hydrogen chloride, in the presence of a carboxylic acid.

In this case, glycerol oligomers which may be partially chlorinated and/or esterificated, are compounds that may be present in the mixture in the use according to the invention. The content of these glycerol oligomers per kg of the mixture containing the chlorohydrin, hydrogen chloride and water, is usually higher than or equal to 1 g, commonly higher than or equal to 10 g, often higher than or equal to 30 g, often higher than or equal to 50 g and frequently higher than or equal to 75 g. That content is usually lower than or equal to 400 g/kg, generally lower than or equal to 300 g/kg, often lower than or equal to 200 g/kg and frequently lower than or equal to 100 g/kg.

In this case, glycerol and glycerol esters are also compounds that may be present in the mixture in the use according to the invention. The content of glycerol (as is and/or in the form of esters), per kg of the mixture containing the chlorohydrin, hydrogen chloride and water, is usually higher than or equal to 1 g, commonly higher than or equal to 5 g, often higher than or equal to 10 g, often higher than or equal to 15 g and frequently higher than or equal to 20 g. That content is usually lower than or equal to 700 g/kg, commonly lower than or equal to 500 g/kg, in many cases lower than or equal to 400 g/kg, generally lower than or equal to 300 g/kg, frequently lower than or equal to 150 g/kg, often lower than or equal to 100 g/kg, specifically lower than or equal to 60 g/kg and in particular lower than or equal to 30 g/kg of the mixture containing the chlorohydrin, hydrogen chloride and water.

The mixture containing the chlorohydrin, hydrogen chloride and water may be single phase or multiphase. This mixture may, for example, contain one or more liquid phases with optionally one or more solid phases in suspension and/or one or more dispersed gaseous phases.

The mixture containing the chlorohydrin, hydrogen chloride and water may be gaseous.

The mixture containing the chlorohydrin, hydrogen chloride and water may be liquid. The mixture containing the chlorohydrin, hydrogen chloride and water is often liquid.

In a first aspect according to the invention, which is preferred, the composition is used as a material for coating an equipment. In this case, at least one part of the surface of the equipment is covered by the coating material. The surface of the equipment which is covered is preferably that which is intended to be in contact with the mixture containing the chlorohydrin, hydrogen chloride and water. This surface may be an internal surface, an external surface or both. The entire surface may be covered with the material. In this aspect, the composition may be an enamel and is preferably an enamel. By enamel, one intends to denote a fused inorganic vitreous superficial coating containing mainly silicon oxide.

In one version of the first aspect, the material for coating the equipment comprises at least two superposed layers, an inner layer and an outer layer, and the outer layer comprises the composition used in the application according to the invention. This outer layer is preferably constituted of said composition.

In this version, the outer layer has a thickness, measured by scanning electron microscopy, which is generally greater than or equal to 0.2 mm, often greater than or equal to 0.4 mm, frequently greater than or equal to 0.6 mm and more specifically greater than or equal to 0.8 mm. This thickness is generally less than or equal to 2.5 mm, often less than or equal to 2 mm, frequently less than or equal to 1.6 mm and more specifically less than or equal to 1.4 mm. A thickness of around 1±0.1 mm is particularly suitable. This layer may be obtained by a single deposition or by several successive depositions.

In this version, the coating preferably comprises an intermediate layer between the surface of the equipment and the outer layer of the coating. The purpose of this intermediate layer is to promote the adhesion of the outer layer to the surface of the equipment to be covered. This intermediate layer generally comprises the same elements as the outer layer but generally in different proportions.

In this version, the matter from which the equipment is formed may be of any type. This material generally contains a metal or a metal alloy. Steel is particularly preferred matter. Steel which are dedicated to be enamelled are convenient matter of equipment.

In a second aspect, the composition is used as a constituent material of the equipment, that is to say that the composition constitutes the material from which the equipment is made.

In the application according to the invention, the term "equipment" is understood to mean containers where compounds are stored, chemical reactions and/or physical operations (rings, support grids and distributor plates equipping distillation columns, reactor) are carried out, tubing, valves, stirring and counter agitators, dip pipes (or siphon pipes) and couplings that connect these containers, parts that ensure leak tightness at these couplings, instruments needed to transfer compounds between the containers, instruments and apparatus for measuring the various parameters needed to control storage (pocket temperature probe, for example), transfer of the compounds and to implementation of chemical reactions and physical operations.

The invention also relates to a process for manufacturing a chlorohydrin comprising several steps, in which a polyhydroxylated aliphatic hydrocarbon, an ester of a polyhydroxylated aliphatic hydrocarbon or a mixture of the two is reacted with a chlorinating agent that contains hydrogen chloride, involving the use according to the invention.

In the chlorohydrin manufacturing process according to the invention, the steps are chosen from the steps of chemical reaction, storage, supply, removal, transfer, chemical treatment or physical treatment of compounds used or produced in the chlorohydrin manufacturing process.

Among the reaction steps, mention may be made of all the reactions that take place during the chlorohydrin manufacturing process such as, for example, during the formation of chlorohydrin, and during the various steps of the process.

Among the storage steps, mention may be made, for example, of storage of the chlorinating agent that contains the hydrogen chloride and storage of the polyhydroxylated aliphatic hydrocarbon, before use, storage of the purges before treatment, storage of the chlorohydrin produced, storage of the catalyst and of its preparations. Among the chemical treatment steps, mention may be made, for example, of a hydrolysis treatment intended to recover the catalyst and a treatment for dissolving the catalyst. Among the physical treatment steps, mention may be made, for example, of operations for separation via stripping, distillation, evaporation, extraction, settling, and filtration, heat exchange, heating and cooling operations.

Among the supply, removal or transfer steps, mention may be made, for example, of operations of recycling, purging and discharging effluents, transport of fluids between the various pieces of equipment in which the chemical reactions, storage and chemical and physical treatments take place.

The chlorohydrin obtained in the process according to the invention may be subjected to a dehydrochlorination reaction to produce an epoxide.

The term "epoxide" is used here to describe a compound containing at least one oxygen bridged on a carbon-carbon bond. In general the carbon atoms of the carbon-carbon bond are adjacent and the compound may contain atoms other than carbon and oxygen atoms, such as hydrogen atoms and halogens. The preferred epoxides are ethylene oxide, propylene oxide, glycidol and epichlorohydrin.

The epoxide is preferably epichlorohydrin and the chlorohydrin is preferably dichloropropanol.

Therefore, the invention also relates to a process for manufacturing an epoxide comprising the process for manufacturing a chlorohydrin according to the invention, followed by a process for dehydrochlorinating the chlorohydrin.

The process for dehydrochlorinating the chlorohydrin may be such as described in WO 2005/054167 in the name of SOLVAY SA, the content of which is hereby incorporated by reference, more specifically the passage from page 19, line 12 to page 22, line 30, in WO 2006/100311 in the name of SOLVAY SA, the content of which is hereby incorporated by reference, more specifically the passages at page 2, lines 22 to 25, and from page 22, line 28 to page 23, line 35, in WO 2008/101866 in the name of SOLVAY SA, the content of which is hereby incorporated by reference, more specifically the passage from page 2, line 1 to page 13, line 16, in PCT/EP2008/057247 in the name of SOLVAY SA, the content of which is hereby incorporated by reference, more specifically the passages from page 9, line 22 to page 13, line 31, in PCT/EP2008/057245 in the name of SOLVAY SA, the content of which is hereby incorporated by reference, more specifically the passages from page 6, line 16 to page 7, line 22 and in PCT/EP2008/059862 in the name of SOLVAY SA, the content of which is hereby incorporated by reference, more specifically the passages from page 1, line 17 to page 10, line 21.

The process for manufacturing the epoxide may be integrated in a global scheme for preparing a chlorohydrin such as described in WO 2006/106155 in the name of SOLVAY SA, the content of which is hereby incorporated by reference, more specifically the passages at page 2, lines 26 to 31, and from page 22, line 10 to page 23, line 19.

The process for dehydrochlorinating the chlorohydrin may also be carried out such as described in WO 2006/100318 in the name of SOLVAY SA, the content of which is hereby incorporated by reference, more specifically the passages at page 2, lines 23 to page 3, line 26, and from page 24, line 17 to page 31, line 18.

The process for dehydrochlorinating the chlorohydrin may also comprise a step of treating water effluents such as described in EP 08150925.9 in the name of SOLVAY SA, the content of which is hereby incorporated by reference, more specifically the passages from page 1, line 18 to page 12, line 10.

The epoxide obtained in the process according to the invention, preferably epichlorohydrin, may be subjected to a reaction with a compound containing at least one active hydrogen atoms in order to produce epoxy resins or glycidyl ethers or glycidyl esters or products usable as coagulants or wet-strength resins or cationizing agents or flame retardants or ingredients for detergents or epichlorohydrin elastomers.

Therefore, the invention also relates to a process for manufacturing epoxy resins comprising the process for manufacturing the epoxide, followed by a process in which the epoxide is subjected to a reaction with a compound containing at least one active hydrogen atom.

Therefore, the invention also relates to a process for manufacturing epoxy resins or glycidyl ethers or glycidyl esters or products usable as coagulants or wet-strength resins or cationizing agents or flame retardants or ingredients fro detergents or epichlorohydrin elastomers, wherein epichlorohydrin is submitted to a reaction with at least one compound selected from monoalcohols, monocarboxylic acids, polyols, polyamines, amino alcohols, polyimides, polyamides, polycarboxylic acids, ammonia, amines, polyaminoamides, polyimines, amine salts, phosphoric acid, phosphoric acid salts, phosphorus oxychlorides, phosphoric acid esters, phosphonic acids, phosphonic acid esters, phosphonic acid salts, phosphinic acids, phosphinic acid esters, phosphinic acid salts, phosphine oxides, phosphines, ethoxylated alcohols, alkylene or phenylene oxides, and mixture of at least two of them, or wherein epichlorohydrin is submitted to a reaction of homopolymerization.

The epichlorohydrin and the uses of epichlorhydrin may be such as described in PCT/EP2008/057247 in the name of SOLVAY SA, the content of which is hereby incorporated by reference, more specifically the passages from page 1, line 18 to page 9, line 21, and from page 31, line 31 to page 63, line 4 and in PCT/EP2008/057246 in the name of SOLVAY SA, the content of which is hereby incorporated by reference, more specifically the passages from page 1, line 24 to page 10, line 14, and from page 13, line 3 to page 44, line 8.

EXAMPLES

The following compositions have been tested. They are made of steel covered with enamel. They have been obtained from the following manufacturers:

TABLE 1

| Composition N° | Manufacturer |
| --- | --- |
| 1 | PFAUDLER Std Dark Blue |
| 2 | DE DIETRICH Std Dark Blue DD 3009 |
| 3 | THALE Std Dark Blue |
| 4 | THALE Light Blue TP 2000 |
| 5 | THALE White |
| 6 | DÜKER |
| 7 | ESTRELLA |

All the contents of the elements in the compositions are in g of element per kg of composition. Those contents have been obtained by X-ray Fluorescence analysis using the lithium tetraborate pearls method.

TABLE 2

| | Compositions (g of element/kg of composition) | | | | | | |
| --- | --- | --- | --- | --- | --- | --- | --- |
| | According to the invention | | | | | Not according to the invention | |
| Element | 1 | 2 | 3 | 4 | 5 | 6 | 7 |
| Na | 77.5 | 100.5 | 82.2 | 89.2 | 84.4 | 98 | 106 |
| Al | 9.6 | <5 | 11.9 | 11.8 | 10.4 | 9.2 | 8.3 |
| Mg | <5 | <5 | 3.7 | <2 | <5 | 6.3 | 2.6 |
| Si | 330 | 314 | 340 | 312 | 307 | 316 | 304 |
| K | 19.2 | 8.1 | 14.4 | 14.9 | 17.1 | 1.9 | 1.7 |
| Ca | 14 | 13.2 | 14.9 | 22.6 | 23.3 | 32 | 32 |
| Ti | <5 | <5 | 5.4 | <2 | <5 | 12 | 14 |
| Co | 6.2 | 7.6 | 7.8 | <2 | <5 | 7.1 | 7.1 |
| Zr | 33.7 | 63.4 | 21.9 | 34.8 | 33.0 | 40 | 44 |
| Ba | 6.3 | 22.4 | <2 | <2 | <5 | <1.4 | <1.4 |
| Fe | 5.4 | <5 | <2 | <2 | <5 | <1.4 | <1.4 |
| Sr | 12.1 | <5 | 4.3 | <2 | <5 | 3.8 | <1.4 |
| Zn | 10.8 | <5 | <2 | <2 | <5 | <1.4 | <1.4 |

Example 1

According to the Invention

In a continuous type process, glycerol, hydrogen chloride and adipic acid have been reacted for around 720 h in a steel reactor covered with enamel so as to generate a mixture containing dichloropropanol, monochloropropanediol, hydrogen chloride and water. The outer enamel layer of the reactor has the composition 1 disclosed in Table 2.

The enamel of composition 1 was shiny before use.

The composition of the enamel of the reactor in contact with the reaction medium comprised, per kg of composition, 77.5 g of Na, 9.6 g of Al, 330 g of Si, 19.2 g of K, 14 g of Ca, 6.2 g of Co, 33.7 g of Zr, 6.3 g of Ba, 5.4 g of Fe, 12.1 g of Sr and 10.8 g of Zn. The composition contained, in addition, magnesium and titanium, each in an amount less than 5 g/kg The composition of the reaction medium averaged over the 720 h of operation comprised, per kg of reaction medium: .

10.8 g of hydrogen chloride, 292.5 g of dichloropropanol, 73.8 g of water, 202.2 g of monochloropropanediol, 21.1 g of dichloropropanol esters, 81.6 g of monochloropropanediol esters, the balance being composed of adipic acid, glycerol, glycerol esters and partially chlorinated and/or esterified glycerol oligomers.

The average pressure was 1.22 bar absolute and the average temperature was 123° C.

After 720 h of operation (±30 days), the enamel composition 1 has remained shiny (visual inspection) which is indicative of the absence of corrosion of the enamel.

Examples 2 and 3

Not According to the Invention

The mixture containing dichloropropanol, monochloropropanediol, hydrogen chloride and water of example 1 has been circulated through equipment parts made of steel covered with enamel, the outer enamel layer of such parts having the compositions 6 and 7 disclosed in Table 2, during all the continuous process of example 1.

The enamel compositions 6 and 7 were shiny (visual inspection) before use.

After 720 h of operation (±30 days), the enamel compositions 6 and 7 have become dull (visual inspection) which is indicative of a corrosion of the enamel.

FIG. 1 top is a picture of the equipment part with enamel composition 6 after the test of example 2. FIG. 1 bottom is a magnification of area (c) of FIG. 1 top.

Area (a) of FIG. 1 is the area of the equipment part protected by a gasket from the contact with the mixture containing dichloropropanol, monochloropropanediol, hydrogen chloride and water.

Area (b) of FIG. 1 is the area of the equipment part in contact with the mixture containing dichloropropanol, monochloropropanediol, hydrogen chloride and water.

Rugosity measurements have been performed on dull and shiny areas of the equipment part with enamel composition 6 using an interferometry microscope. This microscope gives 3D images of the surface analyzed, from which rugosity parameters have been obtained according to Method XP E05-030-1 (AFNOR, French Association of Standardization, December 2003). The surface area analyzed are 224×295 µm corresponding to 736×480 pixels and 112×147 µm corresponding to 736×480 pixels. The rugosity parameters are presented in Table 3.

TABLE 3

| Rugosity parameter | Area (a) (shiny) 224 × 295 µm | 112 × 147 µm | Area (b) (dull) 224 × 295 µm | 112 × 147 µm |
|---|---|---|---|---|
| Ra (nm) | 46.47 | 34.01 | 251.82 | 239.36 |
| Rz (nm) | 673.53 | 312.11 | $3.21\,10^3$ | $6.35\,10^3$ |
| Rpm (nm) | 274.05 | 221.18 | 780.62 | $1.05\,10^3$ |
| Rvm (nm) | −399.48 | −90.94 | $-2.43\,10^3$ | $-5.30\,10^3$ |
| Rq (nm) | 56.62 | 42.29 | 320.74 | 400.29 |
| Surface Index | 1.00038183 | 1.00051701 | 1.03568411 | 1.08317665 |

Ra: arithmetic average deviation of the surface
Rz: maximal amplitude of the surface
Rpm: average maximum surface peak height
Rvm: average maximum surface valley depth
Rq: average quadratic deviation of the surface
Surface index: ratio of the total exposed three dimensional surface area (XYZ) and the lateral surface area (XY). This is a measure of the relative flatness of a surface. A value of 1 means a totally flat surface.

Examples 4 to 8

According to the Invention

Polytetrafluoroethylene bars holding steel bars covered with enamel, with the outer enamel layer having the compositions 1 to 5 disclosed in Table 2, have been placed in an autoclave:

In a liquid mixture comprising, per kg of reaction medium: 20 g of hydrogen chloride, 253 g of dichloropropanol, 100 g of water, 294 g of monochloropropanediol, 5 g of dichloropropanol esters, 80 g of monochloropropanediol esters, the balance being composed of adipic acid, glycerol, glycerol esters and partially chlorinated and/or esterified glycerol oligomers, and In the gas phase above the above liquid mixture.

After 741.5 h, i.e. ~31 days at a temperature of 130° C. and at a pressure of 1.25 bar absolute, the samples have been withdrawn from the autoclave.

The corrosion rates have been obtained by weighing the bars before and after the tests. Those rates are summarized in Table 2.

TABLE 2

| Example | Composition | Corrosion rate (mm/year) | |
| --- | --- | --- | --- |
| | | Gas phase | Liquid mixture |
| 4 | 1 | 0.0052 | 0.0029 |
| 5 | 2 | 0.0044 | 0.0014 |
| 6 | 3 | 0.0033 | 0.0003 |
| 7 | 4 | n.t. | 0.0000 |
| 8 | 5 | n.t. | 0.0030 | n.t.: not tested

The invention claimed is:

1. A method for reducing corrosion of an equipment in contact with a mixture comprising a chlorohydrin, hydrogen chloride and water, said method comprising contacting said equipment with said mixture in a contact region, wherein at least a part of said contact region is coated with a composition that comprises silicon, oxygen, calcium, potassium and titanium or at least a part of said contact region is made of said composition, and wherein silicon is present in said composition in an amount higher than or equal to 235 g of Si per kg of composition, calcium is present in said composition in a positive amount lower than or equal to 25 g of Ca per kg of composition, potassium is present in said composition in an amount higher than or equal to 4 g of K per kg of composition and titanium is present in said composition in a positive amount lower than or equal to 10 g of Ti per kg of composition.

2. The method according to claim 1 wherein the composition comprises potassium in an amount lower than or equal to 60 g per kg of composition, silicon in an amount lower than or equal to 400 g of Si per kg of composition, calcium in an amount higher than or equal to 0.1 g of Ca per kg of composition and titanium in an amount higher than or equal to 0.1 g of Ti per kg of composition.

3. The method according to claim 1 wherein the composition further comprises at least one of the elements selected from the group consisting of sodium, aluminium, magnesium, cobalt, zirconium, barium, iron, strontium and zinc.

4. The method according to claim 1, wherein the ratio between potassium and calcium expressed in equivalent of electrical charges is higher than or equal to 0.05 and lower than equal to 2.

5. The method according to claim 1 wherein at least a part of said contact region is coated with said composition; the composition is an enamel; the coating comprises at least two superposed layers, an inner layer and an outer layer; wherein the outer layer comprises the enamel; and wherein the outer layer has a thickness, measured by scanning electron microscopy, which is greater than or equal to 0.2 mm and lower than or equal to 2 mm.

6. The method according to claim 1, wherein the contacting with the mixture containing a chlorohydrin, hydrogen chloride and water, is carried out under at least one of the following conditions:
 at a temperature higher than or equal to 60° C. and lower than or equal to 200° C.,
 at a pressure higher than or equal to 0.04 bar absolute and lower than or equal to 20 bar absolute, and
wherein the chlorohydrin in the mixture is present as is and/or in the form of esters, the mixture containing
 the chlorohydrin in an amount expressed in moles of chlorohydrin per kg of mixture, greater than or equal to 0.1 and lower than or equal to 8,
 the hydrogen chloride in an amount greater than or equal to 1 g per kg of mixture and lower than or equal to 750 g/kg of mixture,
 water in an amount greater than or equal to 5 g/kg of mixture and lower than or equal to 900 g/kg of mixture, or
 any combinations of two of more thereof.

7. The method according to claim 1 wherein the equipment is selected from containers where compounds are stored, chemical reactions and/or physical operations are carried out, tubing, valves, and couplings that connect these containers, parts that ensure the leak tightness at these couplings, instruments needed to transfer compounds between the containers, instruments and apparatus for measuring various parameters needed to control storage, transfer of compounds or to implementation of chemical reactions and physical operations.

8. The method according to claim 1 wherein the mixture containing the chlorohydrin, hydrogen chloride and water is obtained by reacting a polyhydroxylated aliphatic hydrocarbon, an ester of a polyhydroxylated aliphatic hydrocarbon or a mixture of the two, with a chlorinating agent that contains hydrogen chloride.

9. The method according to claim 8 wherein the chlorohydrin is selected from the group consisting of monochloropropanediol, dichloropropanol and mixtures thereof, and wherein the polyhydroxylated aliphatic hydrocarbon is glycerol.

10. The method according to claim 1, wherein the chlorohydrin is dichloropropanol.

* * * * *

UNITED STATES PATENT AND TRADEMARK OFFICE
CERTIFICATE OF CORRECTION

PATENT NO. : 8,715,568 B2
APPLICATION NO. : 12/681083
DATED : May 6, 2014
INVENTOR(S) : Bobet et al.

Page 1 of 1

It is certified that error appears in the above-identified patent and that said Letters Patent is hereby corrected as shown below:

In the Claims

Column 19, line 31, "The method according to claim 1" should read --The method according to claim 1,--;

Column 19, line 38, "The method according to claim 1" should read --The method according to claim 1,--;

Column 19, line 46, "The method according to claim 1" should read --The method according to claim 1,--;

Column 20, lines 10 and 11, "at a temperature higher than or equal to 60°C. and lower than or equal to 200°C.," should read --at a temperature higher than or equal to 60°C and lower than or equal to 200°C,--;

Column 20, line 26, "The method according to claim 1" should read --The method according to claim 1,--;

Column 20, line 35, "The method according to claim 1" should read --The method according to claim 1,--;

Column 20, line 41, "The method according to claim 8" should read --The method according to claim 8,--.

Signed and Sealed this
Twenty-third Day of September, 2014

Michelle K. Lee
*Deputy Director of the United States Patent and Trademark Office*